United States Patent [19]

Kramer

[11] Patent Number: 5,676,157
[45] Date of Patent: Oct. 14, 1997

[54] DETERMINATION OF KINEMATICALLY CONSTRAINED MULTI-ARTICULATED STRUCTURES

[75] Inventor: James Frederick Kramer, Stanford, Calif.

[73] Assignee: Virtual Technologies, Inc., Palo Alto, Calif.

[21] Appl. No.: 172,868

[22] Filed: Nov. 26, 1993

Related U.S. Application Data

[63] Continuation of Ser. No. 909,570, Jul. 6, 1992, abandoned.

[51] Int. Cl.$^6$ .................................................. A61B 5/103
[52] U.S. Cl. ............................................................ 128/782
[58] Field of Search .................................. 128/782, 781, 128/774; 364/413.02, 400, 559, 815, 816; 342/450, 451, 463, 464, 465; 901/14, 15, 16, 46

[56] References Cited

U.S. PATENT DOCUMENTS

| | | | |
|---|---|---|---|
| 3,868,565 | 2/1975 | Kuipers | 342/450 |
| 3,983,474 | 9/1976 | Kuipers | 364/816 |
| 4,396,885 | 8/1983 | Constant | 324/208 |
| 4,461,085 | 7/1984 | Dewer et al. | 128/782 |
| 4,557,275 | 12/1985 | Dempsey, Jr. | 128/782 |
| 4,986,280 | 1/1991 | Marcus et al. | 128/774 |
| 5,038,137 | 8/1991 | Lloyd | 340/573 |

OTHER PUBLICATIONS

Erdman et al. "Kinematic and Kinetic . . . Instrumentation" Trans. of the ASME. May 1979, vol. 101, pp. 124–134.
Jackson, "Linearity of Radio–Frequency Transducers" Med. and Biol. Eng. and Comput. Jul. 1977, vol. 15 pp. 446–449.

*Primary Examiner*—Guy V. Tucker

[57] ABSTRACT

A prescription is provided which specifies constraints, and the number of joints which may be included between any two position-sensing elements (PSEs), where the joints connect the links of a kinematically constrained multi-articulated structure, whereby the defining parameters of the structure may be determined using the spatial placement of the two PSEs and the kinematic constraints of the multi-articulated structure, and where at least the spatial placement of one link is not directly measured. Also provided are preferred placements of PSEs and goniometers on a kinematically constrained multi-articulated structure which will allow determinatin of the spatial placement of the links, where at least the spatial placement of one link is not directly measured. Revolute joint models of the articulations of the entire human body, as well as preferred PSE and goniometer locations, are provided. An algorithm is provided for determining the joint angles for a finger modeled as a 4-link planar manipulator with one PSE affixed to the fingertip and one PSE affixed to the metacarpus.

6 Claims, 22 Drawing Sheets

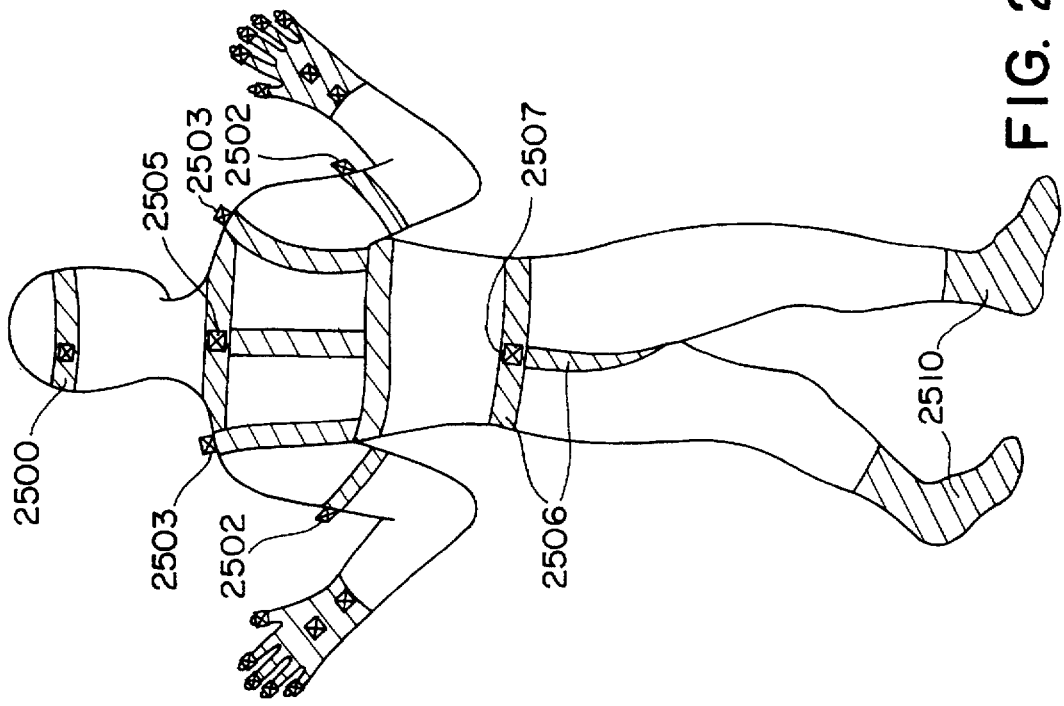
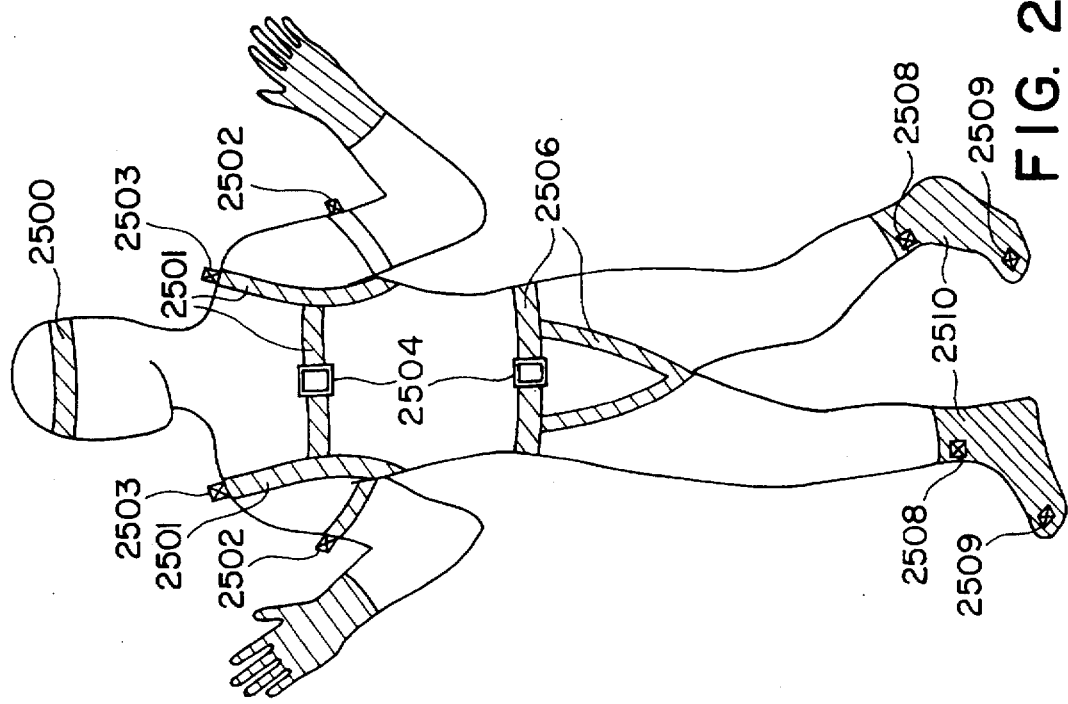

DETERMINATION OF KINEMATICALLY CONSTRAINED MULTI-ARTICULATED STRUCTURES

The application is a continuation of U.S. application Ser. No. 07/909,570, filed Jul. 6, 1992, now abandoned.

Absolute position sensing means has existed for a number of years. In particular, an absolute position sensing technology based on electromagnetic (E/M) sensing has been commercially available since the mid 1970's and comprises two sets of three orthogonally wound coils. One set of three coils is used as the E/M transmitter (Tx) while the other set of three coils is used as the receiver (Rx). One manufacturer of such an E/M system, Polhemus, Inc., drives each of the transmitter coils sequentially at a known frequency, while another manufacturer, Ascension Technology Corp., drives each transmitter coil in pulsed mode. Each receiver coil acts as an antenna and picks up the transmitted E/M signal. Mathematically speaking, driving the coils in this manner produces data for 9 equations (1 equation for each transmitter/receiver coil pair), where there are only 6 unknowns (x, y, z, azimuth, elevation and roll). The 6 unknowns can be determined, to the extent that the sensor may lie in either of two transmitter coil hemispheres.

FIG. 1 shows the configuration of a Polhemus E/M sensing system with 4 Rx's 100 and 1 Tx 101. The Rx's and the Tx, along with the power supply 103 and a communication cable to the computer are connected to the electronics unit 102. The electronic unit sequences and generates the signal transmitted by the Tx and then amplifies, digitizes and otherwise processes the signal received by the Rx's.

There is substantial interest in identifying the spatial placement of various human body-parts in an economic and efficient manner. Up to now no one has accomplished this goal. In the subject application a variety of economical and efficient solutions are provided.

There are a number of intriguing applications which require sensing the spatial placement of various body parts, including sensing of the spatial placement of all body parts simultaneously by a single sensing system. Important applications utilizing measurement of human motion input include: medical hand-evaluation systems to measure post-operative improvement in range of joint movement, or to measure dynamic movement capability of various hand joints; character animation using a hand/body position measurement device to generate a control signal for a graphical marionette or an entire graphical cartoon capable of anthropomorphic movement; human factors/performance evaluation which might, for example, allow simulation of a person getting in/out of a car seat which has been graphically simulated by a computer to test the CAD model of the car for ergonomic design; general Virtual Reality applications which graphically simulate or otherwise utilize the motion input of a human body, e.g., to measure the spatial placement of the elements of the human hand and forearm to generate a cursor emulating the spatial placement of the hand and arm where the cursor is capable of interactivity and/or communication with a virtual object or computer program; and the like.

To put a Rx on every joint of the human body (or other living being) would still require more receivers than is currently possible. Even if it were technically possible, such a complete measurement system would still be very encumbering, heavy and expensive. The focus of the subject invention is to provide methods whereby kinematic constraints of a plurality of body-parts of a human or other living being may be exploited to efficiently reduce the number of sensors required to completely determine the spatial placement (i.e., position and orientation) of relevant body-parts, where the body-parts act as elements of a multi-articulated structure.

RELEVANT LITERATURE

U.S. Pat. Nos. 3,868,565, 3,983,474 and 4,107,858 describe an object tracking and orientation determination means, system and process. "Magnetic Position and Orientation Tracking System," Raab et al, IEEE Trans on Aerospace and Electronic Systems, Vol. AES-15, No. 5, Sept. 1979 provides a review of a commercially available Polhemus E/M position sensing system. *Introduction to Robotics Mechanics & Control* by John J. Craig provides a review of planar manipulators and joint transformations. Commercial product brochures for two commercial manufacturers of E/M position sensors, Polhemus, Inc., and Ascension Technology Corp. describe tracking sensors. "Telepresence Master Glove Controller for Dexterous Robotic End-effectors," Scott S. Fisher, SPIE Vol. 726, Intelligent Robots and Computer Vision: Fifth in a Series (1986), pp. 396–401, provides a glove with flex sensors and an E/M position, sensor. U.S. Pat. No. 4,988,981 provides a glove with flex-sensors and a position sensor. U.S. Pat. No. 5,047,942 provides a glove with variable-resistance strain-sensing flex-sensors.

SUMMARY OF THE INVENTION

The subject invention provides a system comprising sensor configuration means and analysis means whereby the spatial placement (i.e., position and orientation) of the individual elements of a body-part structure comprising a plurality of body parts of a living being (particularly body-parts of a human) may be determined, where at least one element of the body-part structure is not directly measured, e.g., by a position-sensing element, goniometer or translation sensor.

The subject invention particularly focuses on sensing the spatial placement of a body-part structure, which comprises a number of body parts and groups of body parts including but not limited to the following particularly as applied to a human body: the fingers, hand and wrist, the arm, the upper torso, the lower torso, the mid-section, the head and neck, the leg, the foot, a combination of one or more of the above body portions, and the like. One important application is to calculate the spatial placements of links intermediate to the links which are directly measured by a position-sensing element and/or a single-joint position sensor and then reconstruct the spatial placement of the links graphically, where the graphic reconstruction is capable of interactivity and/or communication with a virtual object or computer program.

To make it easier to refer to various body parts and effective articulations, the elements of a body-part structure of interest will be modeled by a combination of links, joints e.g., revolute and prismatic, and the like, where the combination will be generally referred to as a kinematically-constrained multi-articulated structure (KCMAS). The KCMAS to be determined may be a human body or other living body or portion thereof. One or a combination of body portions may yield a KCMAS system, particularly an articulated structure having at least 3, usually at least 4 and often at least 6 related links.

A "link" is a substantially rigid member which may be interconnected to one or a plurality of other links by one or more joints. A "revolute joint" is a joint which allows one link to rotate relative to another link. A "prismatic joint" is a joint which allows one link to translate relative to another link. Typical examples of links of the human body include phalanges of the fingers, the metacarpus, the ulna/radius, humerus, clavicle, neck, spine, pelvis, femur, fibula/tibia, metacarpus, and phalanges of the toes. Typical examples of revolute joints of the human body include the interphalangeal joints of the fingers, the wrist joint, elbow, shoulder, neck, spine, hip, knee, ankle and interphalangeal joints of the toes.

A Position-Sensing Element (PSE) refers to a sensor which provides spatial placement (i.e., x, y, z, roll, pitch, yaw) information. In one embodiment where both a position signal transmitting unit and a position signal receiving unit are needed to provide spatial placement information, the Tx unit and Rx unit are both referred to as PSEs. In some cases, a single PSE may act as both a Tx and Rx. APSE may represent more than one Tx unit and/or more than one Rx unit as commercially available, since some manufacturers limit the number of Rx units that can be used with a single Tx unit to four.

A Single-Joint Position Sensor (SJPS) is a sensor which measures only the rotation or translation a single joint, e.g., a goniometer or translation sensor. A plurality of PSEs and optionally one or a plurality of SJPS may be affixed to the KCMAS and/or affixed to one or more reference locations.

We define the links of the KCMAS which possess an associated PSE and/or SJPS to be "measured links." Likewise, the remaining links of interest which do not possess an associated PSE and/or SJPS (and thus whose spatial placement is not directly measured) are defined to be "unmeasured links." The subject invention provides that at least two links of a KCMAS be measured links (or at least one link be measured relative to a reference link) and at least one link of the KCMAS be an unmeasured link. The kinematic constraints of the KCMAS permit determination of the spatial placement of relevant unmeasured link(s), i.e., which are not explicitly measured.

Typical PSE sensing technologies include but are not limited to Global. Positioning Systems (GPS), Hall Effect and other magnetic and electromagnetic technologies; ultrasonics using time of flight and/or phase information and other acoustic technologies; CCD cameras, lateral effect photodiodes, infrared emitters and detectors and other light-based and optical and imaging technologies; and the like.

Typical goniometric sensing technologies include but are not limited to variable-resistance strain-sensing technologies, electromagnetic technologies, fiber optics, infrared and other light-based tracking technologies, light tubes, potentiometers, encoders, resolvers, rotary Hall Effect sensors, sonar, radar and the like.

Typical translation sensor technologies include but are not limited to LVDT's, electromagnetic technologies, infrared and other light-based tracking technologies, linear potentiometers, linear encoders, proximity sensors, interferometry, sonar, radar and the like.

A preferred embodiment comprises electromagnetic PSEs. Tx's and Rx's used as electromagnetic PSEs may comprise antennae. Tx and Rx antennae may be supported in a variety of non-conducting materials such as cloth, plastic, glass, epoxy, rubber, wood, foam, elastic, clay, plaster and the like. The supported antennae may come in a variety of shapes such as straight (including solid and telescoping), square, circular, spiraled, ellipsoidal, triangular and the like. The antennae may outline space curves, i.e., they need not exist in a plane. The supported antennae may come in a variety of sizes. Tx's and Rx's used as PSEs in a preferred measurement system comprise coils of wire acting as transmitting and/or receiving antennae. Typical coil antennae dimensions are less that 1.0" for Rx's and less than 1.0" for Tx's.

Antennae may comprise wire windings, solid conductive rods, solid conductive sheets, portions of metal, conductive strips and the like. Antennae may also be constructed by photolithography or other forms of etching.

Antennae may be driven directly via wire connection or may be wireless and include a re-radiating "tank" circuit. An antenna employing the tank circuit may receive a first transmitted signal and then re-radiate a second signal to a second receiver, where the re-radiated signal is modified to reflect position information of the re-radiating antenna.

A preferred arrangement is that each electromagnetic PSE contain three coil antennae where each coil comprises planar loops (i.e., each loop existing in a plane) and a normal vector defined parallel to the axis of the loops. The normal is oriented to have one directional component not contained by the plane comprising the normals of the other two coil antennae. A preferred arrangement is further specified where each PSF. comprises three orthogonally placed coil antennae, i.e., the normal of the loops of each coil is perpendicular to the normals of each of the other two coils. A preferred shape for the PSE when three orthogonally placed coil antennae are used, and when each loop is square, is cubical.

A preferred embodiment of a hand and wrist measurement system includes a plurality of Rx units associated with the hand and wrist, each having three orthogonally wound coil antennae with square cross-section (i.e., square loops) ½" on a side housed in a cubical plastic shell filled with epoxy. The preferred embodiment further includes one or a plurality of Tx units, associated with the Rx units, having three orthogonally wound coil antennae with square cross-section 1⅜" on a side and housed in a cubical plastic shell and filled with epoxy. Rx and Tx units of this type are available commercially from Polhemus, Inc. Another preferred embodiment comprises square cross-section Rx coil windings which are ¼" to ⅛" or less on a side.

Antennae may be arranged in groups, e.g., a plurality of coils may be rigidly affixed at various orientations to a single support structure which may be placed about the KCMAS. Antennae may also be arranged individually about the KCMAS. The Tx/Rx antennae may be constructed from wire or etched, and may be coiled, straight, spiral or of a variety of shapes as previously enumerated. An embodiment may include one or a plurality of antennae placed on the top and bottom of a finger or body-part, and/or one or a plurality of antennae placed on the sides of a finger or body-part and/or one or a plurality of antennae placed around a finger or body-part. The antennae may overlap each other and may be non-overlapping, as well as may overlap various elements of the KCMAS.

In some cases, e.g., where the KCMAS is sufficiently constrained or where one or more DOFs is unimportant, a reduced number (as compared to 3 antennae in a preferred embodiment) of antennae may be sufficient. For example, if it is assumed that the fingers can't roll or yaw, then the fingers also can't change one of the positional dimensions. As a result, there are only two positional variables and one orientational variable (e.g., the pitch variable) to be determined. Theoretically, three Tx antennae and one Rx antenna should be sufficient to provide the three equations (one equation for each Tx/Rx pair) necessary to solve for the three variable unknowns.

The subject invention provides means whereby analysis used in the study of simple robotic structures may be adapted to the analysis of more complicated human or other living being motion modeled as kinematically-constrained multi-articulated structures. Furthermore, in accordance with the subject invention, the entire body of the living being to which the body-part structure of interest is a member, is capable of moving relative to a fixed reference frame.

BRIEF DESCRIPTION OF THE DRAWINGS

FIGS. 25A and B are different perspective views of a body harness; and

DESCRIPTION OF THE SPECIFIC EMBODIMENTS

In general, the subject invention provides means for determining the spatial placement of a plurality of human or other living being body-parts. In particular, the subject invention provides means for measuring and determining the spatial placement of a human hand system including various elements of the hand, wrist and forearm.

Figure 2A:
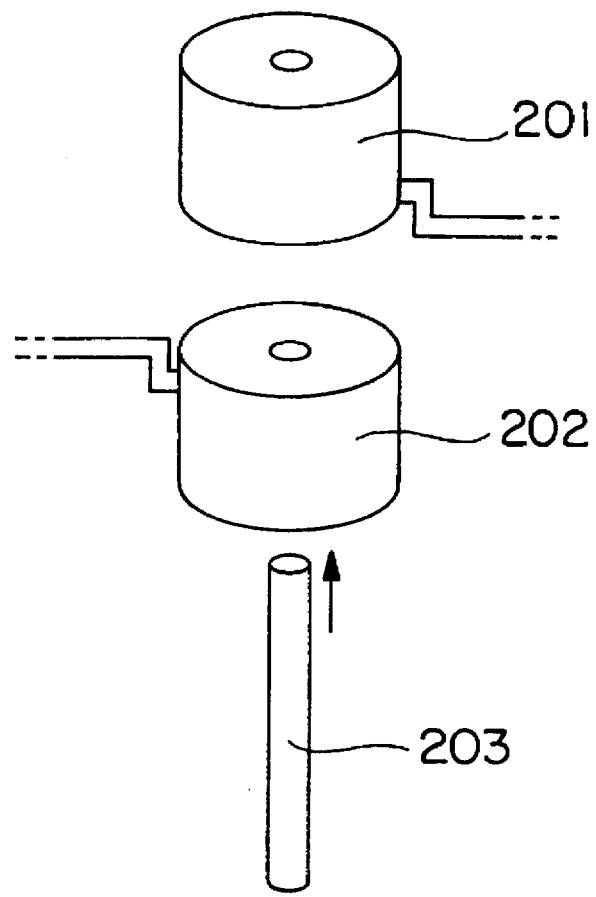
FIGS. 2A and 2B are enlarged views of a model for a revolute joint, with 2A the top and 2B the bottom of the cylindrical joint.
Figure 2B:
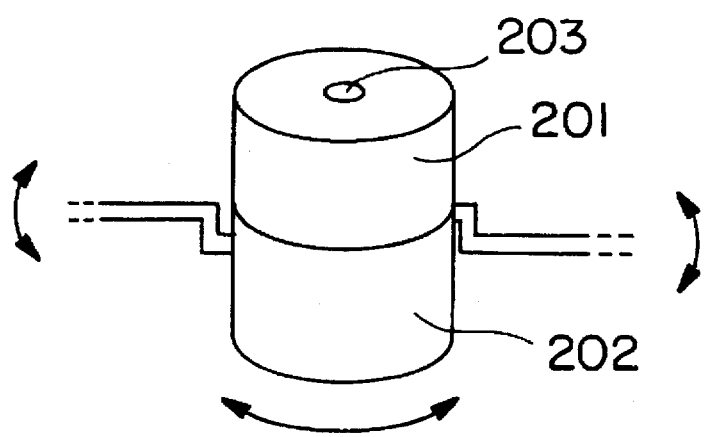

Referring now specifically to the drawings, FIGS. 2A and 2B show enlarged views of a model for a revolute joint. A Revolute joint is depicted as a cylindrical joint having two cylindrical hinged elements 201, 202 and a coaxial axis of rotation, where one hinged element is capable of rotating about the axis relative to the other hinged element. In FIGS. 2A and 2B the top 201 and bottom 202 portions of the cylinder may rotate about the axis 203 relative to each other. When more than one rotary degree-of-freedom (DOF) is specified at a single location, multiple cylinders are drawn, one cylinder per DOF. Except when indicated otherwise, when two Revolute joint cylinders are drawn affixed to each other at a right angle, the intent is that the axes of rotation intersect and the joint is effectively a "Universal Joint" ("U-joint"). In addition, except when indicated otherwise, no line will be drawn to show the separation between hinged elements of a cylinder about the hinge axis.

As previously mentioned, to make it easier to refer to various body parts and effective articulations, the elements of the body-part structure of interest will be modeled by a combination of links, revolute joints, prismatic joints and the like. The combination of articulated body-parts will be generally referred to as a kinematically-constrained multi-articulated structure (KCMAS).

Figure 3:
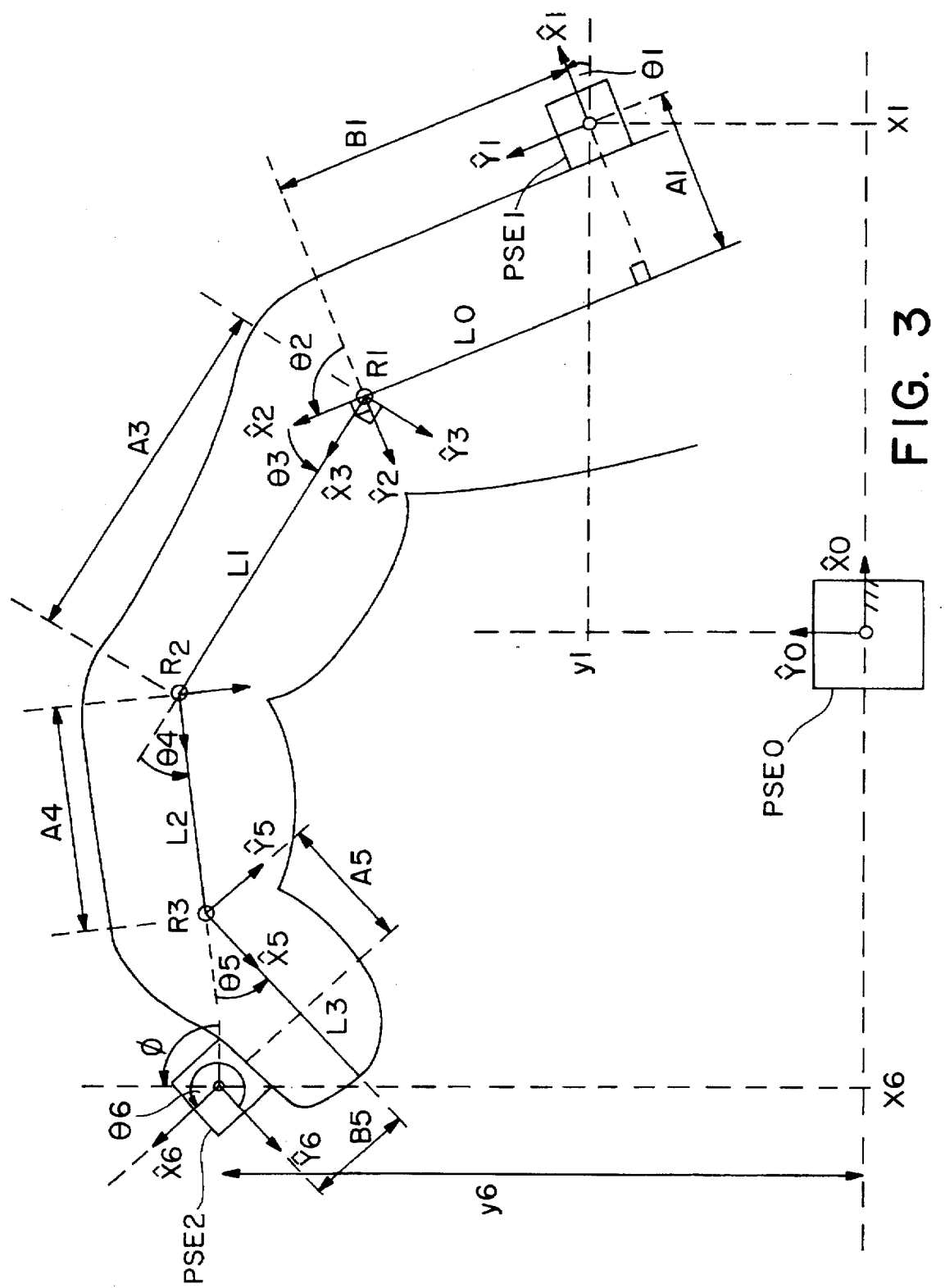
FIG. 3 is an illustration of the kinematics of a human palm and finger.

FIG. 3 is exemplary of the kinematics of a human palm and finger modeled as a 4-link planar KCMAS. The calculations provided below are exemplary of a mathematical process for determining the spatial placement of the phalanges of a human finger given knowledge of the spatial placement of the fingertip relative to the metacarpus. In general, the link/joint model provided by FIG. 3 along with the associated calculations are exemplary of the process for determining the spatial placement of a class of body-parts modeled as KCMASs for which a single 6 degree-of-freedom measurement (i.e., x, y, z, roll, pitch, yaw) of a link at one location on the articulated structure relative to a link at a second location on the structure may be used to completely specify the spatial placement of intermediate links.

Since the number of PSEs may be reduced from the more obvious placement of one PSE per link, complexity, inertia, weight, incumbering nature and cost of the measurement system may be reduced.

Figure 4:
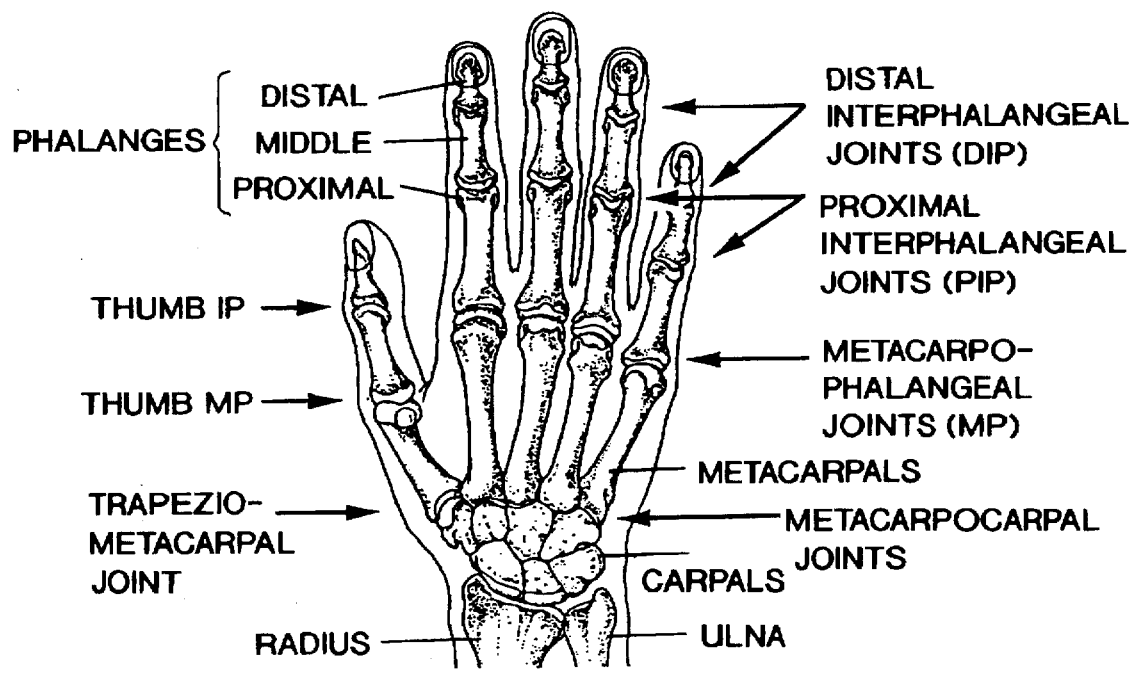
FIG. 4 is an anatomical description of the human hand.

In FIG. 3, the entire metacarpus (palm) is defined as a single link, L0, the proximal phalanx is defined as L1, the medial phalanx is defined as L2 and the distal phalanx is defined as L3. Revolute joints R1, R2 and R3 are assumed to have parallel axes and connect links L0, L1, L2 and L3 as shown. In accordance with a preferred embodiment, PSE0 is affixed to a base reference location which does not rigidly follow the movement of the hand structure to be measured and is preferably unconnected with the hand structure. Further in accordance with said preferred embodiment, PSE1 is affixed to L0 (the, metacarpus) and PSE2 is affixed to link L3 (the distal phalanx). FIG. 4 provides the naming convention used for the various elements of the fingers, hand and wrist.

To facilitate the mathematical determination of the spatial placement of unmeasured links and to be able to quantitatively talk about orientations and positions of PSEs and SJPSs, as well as links and joints, we define a reference frame associated with each link. Subsequent distances and angles are defined between one or more axes of the frames. The origin of a PSE (e.g., Tx or Rx) is defined as the position and orientation such that when the origin of a Rx PSE is located at the origin of the associated Tx PSE, the position and orientation parameters specifying the spatial placement of the Rx relative to the Tx all have a value of zero.

When Tx's and Rx's are used as PSEs, there are various possible Rx/Tx assignments for PSE0, PSE1 and PSE2. In one preferred embodiment PSE1 and PSE2 act as Rx's and PSE0 acts as a Tx. The reason for these Tx/Rx assignments is that present commercial Tx's are normally larger, heavier and generate considerably more heat than Rx's while in operation. Therefore, it is ergonomically preferred to use the smaller, lighter, cooler Rx's on the body-part and keep the Tx's separate from the body whenever possible. A signal transmitted from PSE0 to PSE1 would allow determination of the spatial placement of the metacarpus relative to PSE0. PSE2, acting as a Rx, could also receive a signal transmitted from PSE0, which would allow determination of the spatial placement of PSE2 relative to PSE0. From the spatial placements of PSE1 and PSE2 relative to PSE0, the spatial placement of PSE2 relative to PSE1 is determined and, hence, the spatial placements of the links between PSE2 and PSE1 may be determined as described below.

In another embodiment provided by FIG. 3, PSE1 may act as both a Rx and a Tx. A data processor provides means to switch between driving an antenna with a signal when acting as a Tx, and then amplifying the signal received by the antenna when acting as a Rx. For example, the same antennae of PSE1 utilized as antennae receiving a signal from PSE0 may subsequently act as transmitting antennae which transmit a signal to PSE2. One advantage of this embodiment is that in many instances, PSE1 will be located closer to PSE2 than will be PSE0, hence, PSE1 may comprise a physically smaller antenna and may transmit lower power signals. Since lower power signals are needed, heat generation from PSE1 located in juxtaposition to the metacarpus won't present a problem. In addition, the signal received by PSE2 from a close-by PSE1 may be more accurate, e.g., less corrupted by noise, than a signal received by PSE2 from the more distant PSE0. This principle for dual usage of a PSE as both a Rx and Tx may be employed for other KCMASs. It finds advantages whenever neighboring PSEs are closer to each other than the PSEs are to an external reference PSE. The principle may be used multiply where a first PSE transmits a signal to a second PSE, the second PSE transmits a signal to a third PSE, the third PSE transmits a signal to a forth PSE, and so forth.

Referring again to FIG. 3, the base reference frame is denoted Frame 0 and is located at the origin of PSE0. PSE1 is affixed to L0 but the origin of the reference frame assigned to PSE1 is offset from the L0 link axis by a perpendicular distance, A1. The distance from PSE1 to R1 as measured along the link axis is B1. Similarly, PSE2 is offset from the link axis L3 by a perpendicular distance B5. The distance from PSE2 to R3 as measured along the link axis is A5. The distances from R1 to R2 and from R2 to R3 as measured along link axes L1 and L2 are A3 and A4 respectively. In FIG. 3, an angle theta-i (e.g., angles theta1–theta6, i.e., Th1–Th6) is measured between the X-axis of Frame (i-1) and the X-axis of Frame i, where the measurement is taken about the Z-axis. Angle Phi represents the angle between the X-axis of Frame 0 and the X-axis of Frame 6 as measured about the Z-axis. (x1, y1) are the coordinates of Frame 1 measured in Frame 0. (x6, y6) are the coordinates of Frame 6 measured in Frame 0.

There are various methods which can be used to solve the "4-link finger" example KCMAS of the subject invention.

Below only one solution technique is provided, but presents a general framework which may be suitably adapted to provide a solution to related problems. The technique presented below produces an algebraic solution adapted from [Craig 1986], whereas other approaches, e.g., a geometric approach, may also be adapted. The mathematical solution provided and the example of the 4-link finger are chosen to exemplify how the spatial placement of unmeasured links may be determined by measuring certain selected links and utilizing the kinematic constraints of a multi-articulated structure. The solution and example provided are not intended to limit the scope of applications nor the mathematical solution methodology. Appropriate alternate mathematical solution techniques and/or adaptations of the presented technique may be used to solve for the defining parameters of a kinematically constrained multi-articulated structure.

Figure 5:
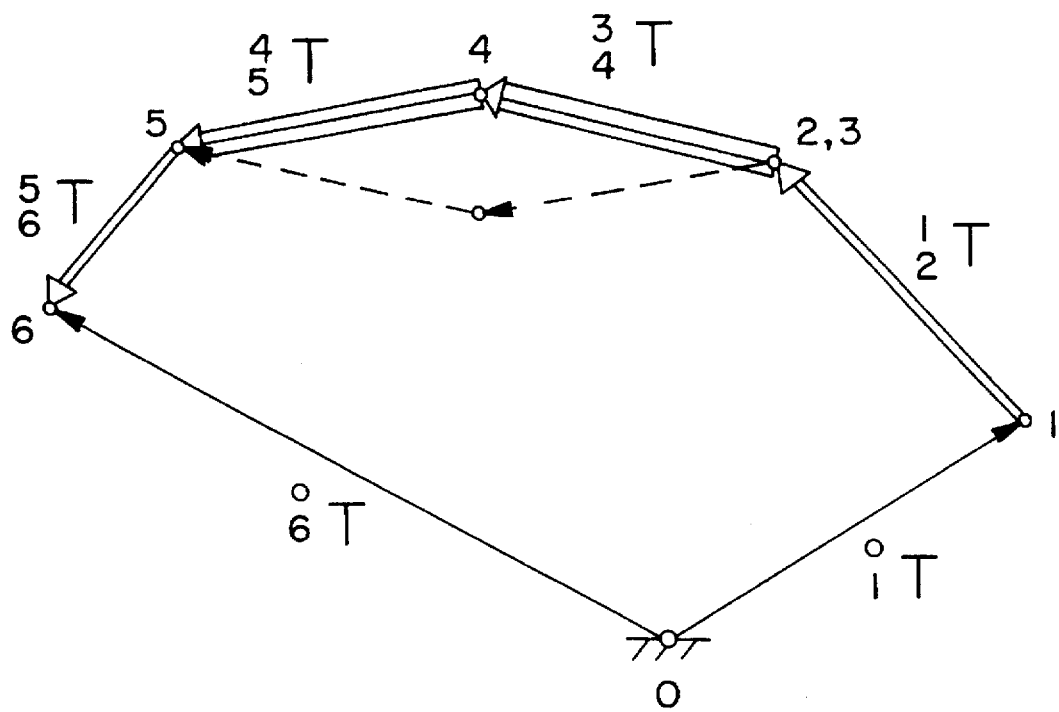
FIG. 5 is a vector representation of the "4-link" class of problems.

To provide a mathematical shorthand for representing the coordinates of a first reference frame relative to a second frame, we adopt the notation $[i-1,i]T$ to denote the transformation from Frame (i-1) to Frame (i). FIG. 5 provides a vector representation of the transformation $[i-1,i]T$, and specifically provides the vector representation of the "4-link" class of problems. The tail of the vector represents the origin of the frame the transformation is from, the head of the vector represents the origin of the frame the transformation is to, and the length of the vector represents the distance between the frame origins. Rules for vector addition and subtraction apply so one can see how to determine one transformation based on combinations of transformations. Note that negating a vector is equivalent to inverting a transformation. The triple-line vectors represent the spatial placement of the two unmeasured links, the single-line vectors represent the measured links, and the double-line vectors represent transformations which are known via the geometry of the structure.

As can be seen from the vector diagram there is a second possible placement of the unknown vectors that would allow the lengths of the vectors to remain the same lengths and yet be consistent with the rest of the vector diagram. The alternate vectors are drawn with dashed lines. This second vector solution corresponds to hyperextension of the PIP joint, whereas the "triple-line" solution corresponds to normal flexion of the PIP joint. The solution for normal PIP flexion is typically chosen, unless there; is a special exception or unless an algorithm for determining between the two solutions is used which utilizes information such as knowledge of the maneuver or task the hand is performing, and/or which utilizes position and dynamic information of neighboring joints and links.

A mathematical description using the transformation shorthand previously defined follows:

Measured: $[0,1]T$, $[0,6]T$ (Actually, x0, y0, Th1, x6, y6, Phi measured, assuming that PSE0 is a Tx and PSE1 and PSE2 are Rx's.)

Known: $[1,2]T$, $[5,6]T$

Unknown: $[4,5]T$, $[3,4]T$, $[2,3]T$ (Actually, Th3, Th4, Th5 unknown.)

We write the "Transformation Equation" as $$[0,6]T = [0,1]T * [1,2]T * [2,3]T * [3,4]T * [4,5]T * [5,6]T$$

Solving for $[2,5]T$ we get $$[2,5]T = ([0,1]T * [1,2]T)^{-1} * [0,6]T * [5,6]T^{-1}$$

We now provide the mathematical description for $[2,5]T$ in terms of homogeneous transformations. As additional shorthands we use ci to denote cos(theta_i) and cijk to denote cos(theta_i+theta_j+theta_k). Similarly, si denotes sin(theta_j) and sijk denotes sin(theta_i+theta_j+theta_k). cPh denotes cos(Phi) and sPh denotes sin(Phi). cPs denotes cos(Psi) and sPs denotes sin(Psi).

The following are the homogeneous transformation matrices needed for our analysis.

Measured:

$$[0,1]T = \begin{matrix} c1 & -s1 & 0 & x1 \\ s1 & c1 & 0 & y1 \\ 0 & 0 & 1 & 0 \\ 0 & 0 & 0 & 1 \end{matrix}$$

$$[0,6]T = \begin{matrix} cPh & -sPh & 0 & x6 \\ sPh & cPh & 0 & y6 \\ 0 & 0 & 1 & 0 \\ 0 & 0 & 0 & 1 \end{matrix}$$

Known:

$$[1,2]T = \begin{matrix} 0 & -1 & 0 & -a1 \\ 1 & 0 & 0 & b1 \\ 0 & 0 & 1 & 0 \\ 0 & 0 & 0 & 1 \end{matrix}$$

$$[5,6]T = \begin{matrix} 0 & 1 & 0 & a5 \\ -1 & 0 & 0 & b5 \\ 0 & 0 & 1 & 0 \\ 0 & 0 & 0 & 1 \end{matrix}$$

Unknown:

$$[2,3]T = \begin{matrix} c3 & -s3 & 0 & 0 \\ s3 & c3 & 0 & 0 \\ 0 & 0 & 1 & 0 \\ 0 & 0 & 0 & 1 \end{matrix}$$

$$[3,4]T = \begin{matrix} c4 & -s4 & 0 & a3 \\ s4 & c4 & 0 & 0 \\ 0 & 0 & 1 & 0 \\ 0 & 0 & 0 & 1 \end{matrix}$$

$$[4,5]T = \begin{matrix} c5 & -s5 & 0 & a4 \\ s5 & c5 & 0 & 0 \\ 0 & 0 & 1 & 0 \\ 0 & 0 & 0 & 1 \end{matrix}$$

To solve the kinematically constrained multi-articulated structure we equate two expressions for [2,5]T obtained from the vector diagram of FIG. 5:

$$[2,5]T = [2,3]T * [3,4]T * [4,5]T \quad\quad 1.$$

$$[2,5]T = [0,1]T * [1,2]T)^{-1} * [0,6]T * [5,6]T^{-1} \quad\quad 2.$$

By multiplying out the three homogeneous transformations of the first equation for [2,5], we get $$[2,5]T = \begin{matrix} c345 & -s345 & 0 & (a4*c34+a3*c3) \\ s345 & c345 & 0 & (a4*s34+a3*s3) \\ 0 & 0 & 1 & 0 \\ 0 & 0 & 0 & 1 \end{matrix}$$

We cannot completely multiply out the second equation for [2,5]T since until we have measured values for theta1, x1 and y1, and know the structure dimensions a1, b1, a5, and b5, we cannot invert the specified matrices. However, since we do know the structure is a planar system, we can assume the following final form:

$$[2,5]T = \begin{matrix} cPs & -sPs & 0 & x \\ sPs & cPs & 0 & y \\ 0 & 0 & 1 & 0 \\ 0 & 0 & 0 & 1 \end{matrix}$$

Equating elements we get $$cPs = c345 \quad\quad a.$$

$$sPs = s345 \quad\quad b.$$

$$x = a4*c34 + a3*c3 \quad\quad c.$$

$$y = a4*s34 + a3*s3 \quad\quad d.$$

These are four nonlinear equations in 3 unknowns (Th3, Th4, Th5). The results are summarized below:

$$Th3 = \arctan 2(y, x) - \arctan 2(a4*s2, a3+a4*c4)$$

$$Th4 = \arctan 2(s2, c2)$$

$$Th5 = \arctan 2(sPs, cPs) - Th3 - Th4$$

where $$c2 = (x^2 + y^2 - a3^2 - a4^2)/(2*a3*a4)$$

$$s2 = -or + (1-c2^2)^{-\frac{1}{2}}$$

where the two signs provide the flexion and hyperextension solutions of joint 4.

Arctan 2(x, y) computes $\tan^{-1}(y/x)$ while using the signs of both x and y to determine the quadrant in which the result lies.

FIGS. 6–9 provide examples of limitations of the links and joints located between two points of known relative spatial placement on a general KCMAS whereby the spatial placement of each link may be uniquely determined using kinematic constraints. In the figures the pitch, yaw and roll joints are assumed to be revolute joints.

Figure 10:
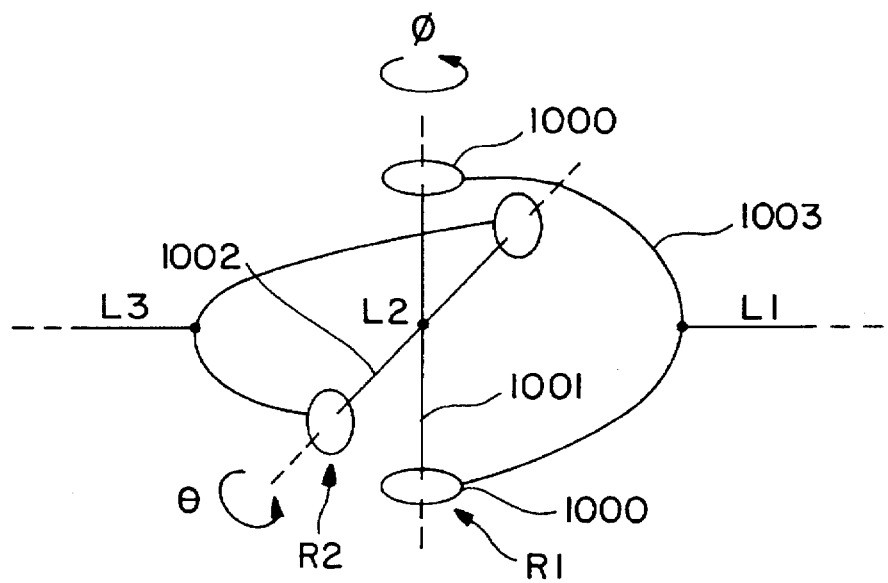

In FIGS. 6–9, when a pitch and yaw joint are to be drawn perpendicular to each other with their axes intersecting, a schematic drawing designating a U-joint, such as provided by FIG. 10, will be used. In FIG. 10, the two loops 1000 drawn on the ends of the single straight axis 1002 form a hinged joint R1 about which the adjoining straight line axis 1001 is able to rotate. The curved line 1003 represents a rigid joining of the two loops, where the curved line also represents one end of a link. The straight axis 1009 between the two loops is rigidly affixed at a right angle to another straight axis 1002 of a similarly hinged mating joint/link structure R2, where the two axes form link, L2. Note that when axis xx 1001 is rotated +90 or −90 degrees, axis xx 1002 aligns with link L1.

Figure 6:
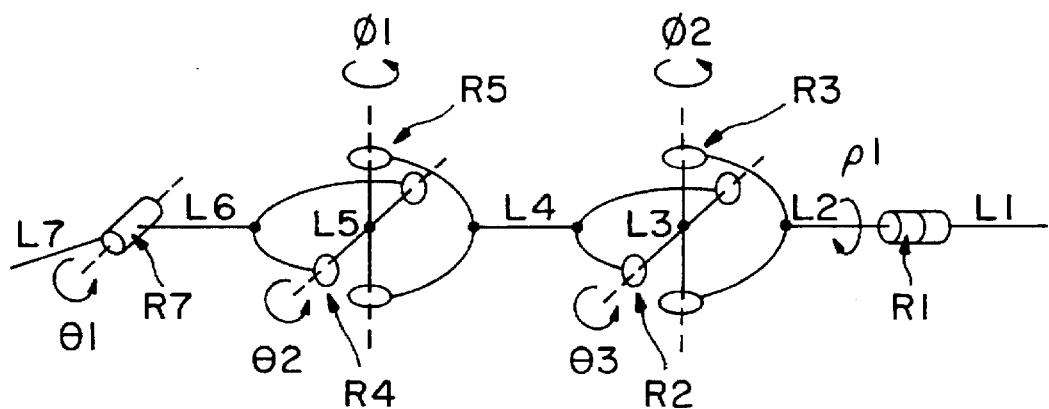
FIGS. 6 to 10 are illustrations of examples of links and joints located between two points of known relative spatial placement on a general KCMAS.
Figure 7:
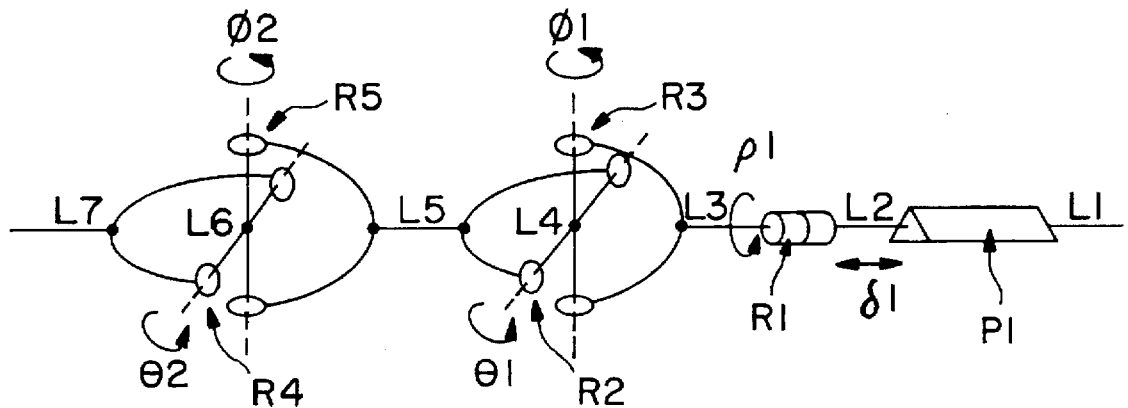
Figure 8:
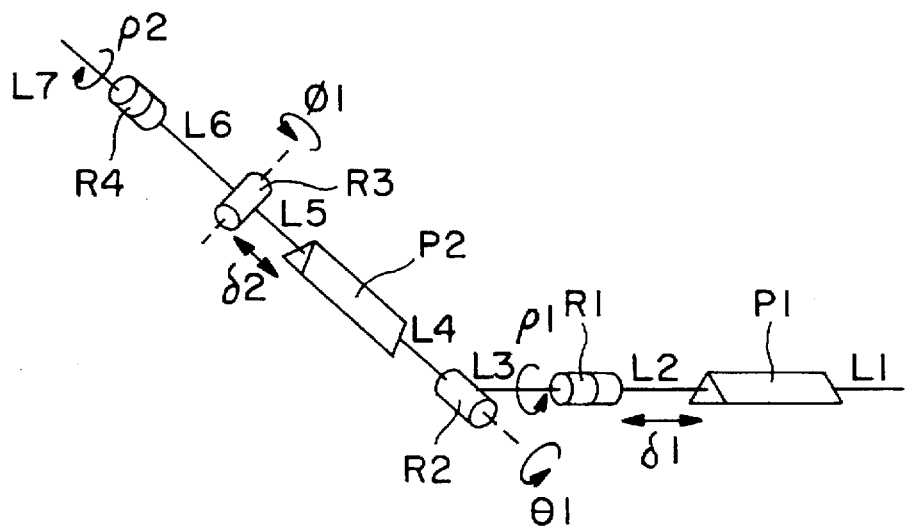
Figure 9:
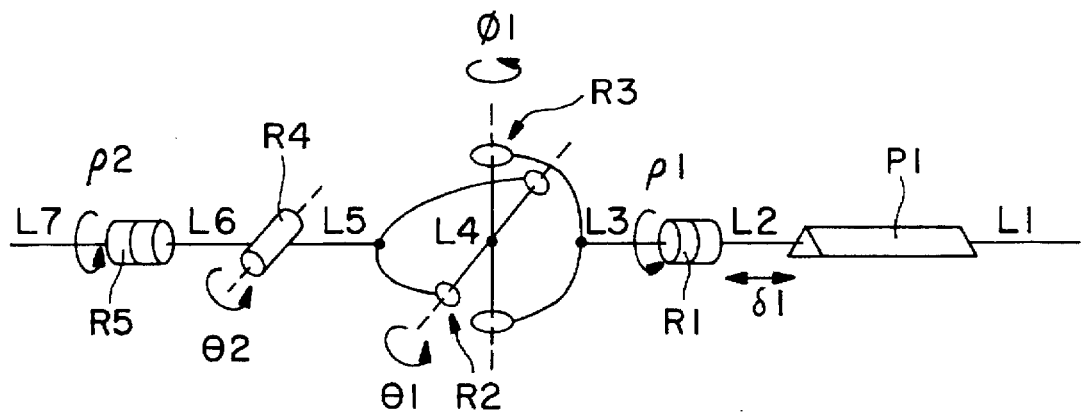

FIG. 6 provides an example where at most three unknown pitch joints (R2, R4, R7), at most two unknown yaw joints (R3, R5) and at most one unknown roll joint (R1) may exist between two points of known relative spatial placement (e.g., on L1 and L7) for the spatial placements of intermediate links (e.g. L2–L6) to be uniquely determined. For this combination the middle pitch joint R4 is limited to [0, 180) degrees (e.g., no hyperextension) and the two yaw joints are limited to (31 90, 90) degrees, otherwise a pitch joint axis may align with the roll joint axis and render the KCMAS indeterminant. In general, any time there are three unknown parallel Revolute joints, the middle joint must be limited to (−90, 90) degrees for the spatial placements of the joints to be uniquely determined. Equivalently, the pitch and yaw joints of FIG. 6 may be interchanged such that the embodiment includes three unknown yaw joints, two unknown pitch joints and one unknown roll joint, where the middle yaw joint is limited to [0, 180) degrees.

Note, if the U-joint symbol of FIG. 10 were rotated 90 degrees about the L1 axis, the (−90, 90). degree limitations would apply to the pitch joint. Since it is very difficult for humans to abduct a finger +90 or −90 degrees but can pitch some joints +90 or −90 degrees, the U-joint orientation is selected as shown in FIG. 10, where 1001 is the yaw axis and 1002 is the pitch axis.

In general there can never be four unknown parallel revolute joints between points of known relative spatial placement on a KCMAS for the spatial placements of the elements of the structure to be uniquely determined. If there are three unknown pitch joints and at least one: unknown yaw joint, where the perpendicular pitch and yaw joint axes do not intersect but have a connecting line, LX, of non-zero link length, then if yawed +90 or −90 degrees, LX becomes a fourth unknown pitch joint and thus the structure is indeterminant. One solution is to add a goniometer to one of the pitch joints so only three pitch joints are unknown between the, two points of known relative spatial placement on the KCMAS.

In partial summary, the spatial placements of the elements of a KCMAS between two points of known relative spatial placement may be uniquely determined for a KCMAS comprising at most six unknown joints, where:

(1) at most one unknown roll joint, and
  (a) no unknown prismatic joints, and
  (b) at most three unknown pitch joints, and
  (c) at most two unknown yaw joints
  or
  (b) at most two unknown pitch joints, and
  (c) at most three Unknown yaw joints
or
(2) at most one unknown roll joint, and
  (a) at most one unknown prismatic joint, and
  (b) at most two unknown pitch joints, and
  (c) at most two unknown yaw joints
or
(3) at most two unknown roll joints, where the axes for the roll joints and an unknown pitch joint axis and an unknown yaw joint axis do not all four intersect at a single point, and
  (a) at most one unknown prismatic joint, and
  (b) at most two unknown pitch joints, and
  (c) at most one unknown yaw joint
  or
  (b) at most one unknown pitch joint, and
  (c) at most two unknown yaw joints
or
(4) at most two unknown roll joints, where the axes for the roll joints and an unknown pitch joint axis and an unknown yaw joint axis do not all four intersect at a single point, and
  (a) at most two unknown prismatic joints, where the prismatic joint axes are not parallel, and
  (b) at most one unknown pitch joints, and
  (c) at most one unknown yaw joint The notes about the consequences of yawing +90 or −90 degrees must still be observed.

If the number of unknown joints that exist between two points of known relative spatial placement exceed the maximum number allowable as indicated above, SJPSs may be used to measure one or more joints as necessary to bring the unknown number of joints down to within the prescribed limit. A goniometer may be used to measure the rotation of each revolute joint in excess of the prescribed maximum number allowable revolute joints. Similarly, a translational sensor should be used to measure the translation of each prismatic joint in excess of the prescribed maximum number of allowable prismatic joints.

Since the subject invention provides means for determining the spatial placement of various unmeasured links of a KCMAS, situations may arise where the spatial placement of the measured links may require a DOF or link length inconsistent with the modeled structure. In mathematical terms, the required solution may not exist in the achievable domain of the structure. A first example of such a situation is when there is a slight yaw measured by the PSE, where there is no yaw DOF in the model. A second example difficulty may arise when all links are fully extended and the PSE on the measured link yields a value which would require an increase in one or more link lengths.

A simple solution to the problem of PSE data being inconsistent with attainable link geometry is to employ a "pre-processor" algorithm which first modifies the PSE measurement so it lies within the attainable domain of the structure before trying to determine the spatial placements unmeasured links. In the first example above, the pre-processor may require that all non-zero yaw values from the PSE be ignored. In the second example above, the pre-processor may require the overall length measurement to be truncated to a distance which can be reached by the KCMAS.

The method for finding a solution to a structure with inconsistent data may involve determining the attainable placement of links which most closely fits the measured data, where "most closely" is as measured by a specified distance measure. An example distance measure is the weighted sum of squares of errors in spatial placement data of the measured link, i.e., $$\text{Dist}(L, L_m) = a*(x-x_m)^2 + b*(y-y_m)^2 + c*(z-z_m)^2 + d*(Y-Y_m)^2 + e*(P-P_m)^2 + f*(R-R_m)^2,$$

where L=link placement determined via calculation, $L_m$=link placement determined as measured, x=x-coordinate, y=y-coordinate, z=z-coordinate, Y=yaw angle, P=pitch angle, R=roll angle, the lowercase "m" signifies "measured" coordinates of the measured link, and non-subscripted variables signify "calculated" coordinates of the measured link as determined by the trial solution of all links.

Other solutions to the problem of inconsistent PSE data may involve an algorithm for adding artificial DOFs as necessary at various locations throughout the intermediate joints and links to account for the inconsistency. An algorithm may also account for the inconsistent portion of the measurement by modifying a single joint or link (e.g., modifying link length, if the inconsistency takes the form of a constant offset), or may evenly modify each joint and link, or may modify the joints and links in a proportion to the link length, or the algorithm may involve an optimization technique for modifying the joints and links that may be modified the least yet "absorb" the inconsistency.

Figure 11:
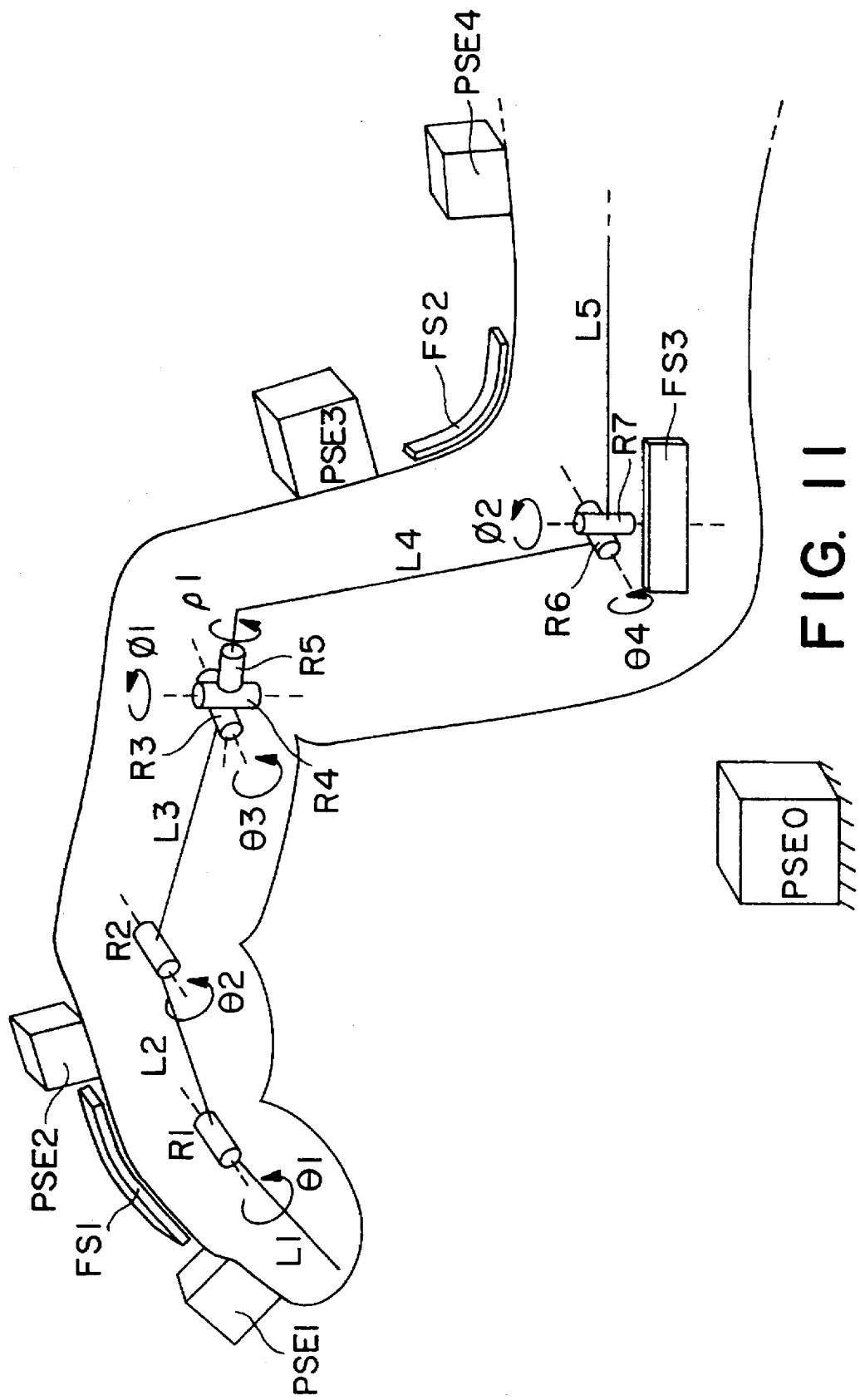
FIG. 11 is a side view of a link/revolute joint of a human hand, wrist and forearm.

FIG. 11 shows a side view of a link/revolute joint model of a human hand, wrist and forearm. While only one finger is shown, the concept provided may be repeated for multiple fingers. Note that there are now three Revolute joints provided to model the metacarpophalangeal (mcp) joint. In addition to the single revolute mcp joint described in the example of FIG. 3 (which is now labeled as R3 and about which angle Th3 is measured), revolute joint R4 has been added to model the abduction/adduction capability (Phi1) of the finger, and R5 to model the roll/rotation capability (Rho1). The two added will not prevent Th1, Th2, Th3, Phi1 and Rho1 from being uniquely determined as long as the relative spatial placements of PSE1 and PSE3 are known. In other words, knowing the spatial placements of PSE1 and PSE3, along with the kinematic constraints of the human hand (e.g., no hyperextension of the proximal interphalangeal joint) Th1, Th2, Th3, Phi1 and Rho1 are uniquely specified.

Without R4 and R5, the same method of solution used in the example of FIG. 3 may be used. Since only one lateral motion DOF (R4) is being added, then any abduction of the finger relative to the metacarpus sensed by PSE1 or PSE2 must be attributed to a yaw of Phi1 about the R4 axis. Likewise, only one roll DOF (R5) has been added, so any roll of the finger relative to the metacarpus (PSE3), must be attributed to a roll of Rho1 about R5. Once Phi1 and Rho1 are determined, they can be used to transform a frame located at the origin of PSE3 to a frame affixed to R3 and aligned with L3, just as Frame 3 was affixed to R1 and aligned with L1 in the example of FIG. 3. With the frame thus transformed to R3, the problem is again to solve the same 4-link planar problem as in the example, where the unknown angles are now labeled Th3, Th2 and Th1.

FIG. 11 provides various configurations of PSEs which may be used to completely determine the spatial placement of the relevant elements of the hand and wrist. By employing PSE0, PSE1 and PSE3, all joint parameters of a finger may be determined as described above. By the addition of PSE4, the values of pitch and yaw (Th4 and Phi2) of the two modeled wrist joints, R6 and R7 respectively may be determined. The use of PSE0, PSE1, PSE3 and PSE4 produces a preferred embodiment.

There are various other preferred embodiments that have their own advantages and disadvantages. For example, in another preferred embodiment PSE2 is employed in place of PSE1, hence, the finger experiences lower inertial forces, less weight, and the PSE is less likely to get in the way when picking up small objects such as a needle on a table. Additionally, PSE2 may be more easily affixed to the medial phalanx than PSE1 is affixed to the distal phalanx, determinations of Th2 and Th3 will be less noisy since any noise in the measurement of PSE2 relative to PSE3 will be spread over fewer links and joints, and it will be less likely that the means for affixing PSE2 will hinder fingertip tactile sensitivity, unlike the means for affixing PSE1.

The obvious disadvantage of replacing PSE1 with PSE2 is that the spatial placement of L1 is now not determined. One method to determine the spatial placement of L1 is to infer it from a polynomial relationship that estimates the natural coupling of the PIP and DIP joints. For example, if nothing is in contact with the fingertip, any conscious flexing of the PIP joint produces a subconscious flexing of the DIP joint. If the fingertip comes into contact with an external object, this natural coupling of the two joints can be altered.

If it is likely that the fingertip will come into contact with an object and the spatial placement of the distal link is desired, a goniometer (i.e., general angle sensor) may be used. A preferred embodiment where a goniometer is used in addition to PSEs comprises variable-resistance strain-sensing flex sensors to act as goniometers. Other suitable goniometric sensing technologies may be used, such as fiber optics, light tubes, potentiometers, encoders, resolvers, rotary Hall Effect sensors and the like. A typical variable-resistance strain-sensing flex sensor is 1¼" long, ⅛" wide and 3 mil high. For a detailed description of such a flex sensor, refer to U.S. Pat. No. 5,047,952 of Kramer, et al.

Figure 1:
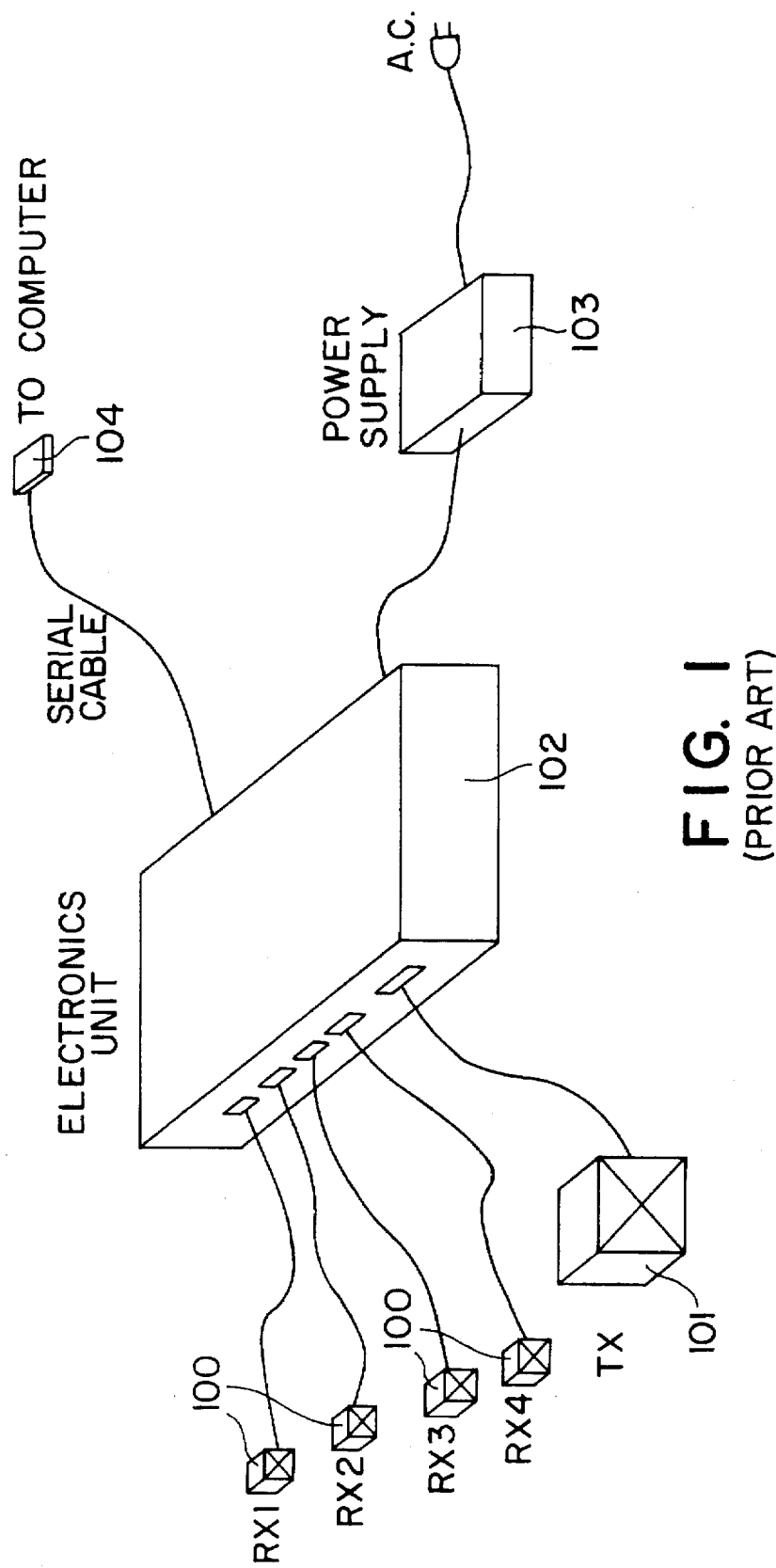
FIG. 1 is a Polhemus E/M sensing system with four Rx's and one Tx.

FIG. 11 also provides various locations on the hand and wrist for goniometers, specifically flex-sensors. A preferred hand-sensing system includes PSE0, PSE2, PSE3, PSE4 and FS1 as shown in FIG. 11. The goniometer, FIG. 1 is used to directly determine angle Th1. The spatial placement of L2 is determined from PSE2 and so the spatial placement of L1 is easily determined.

It may be desired that the kinematic model of the hand include capability for the metacarpus to arch, such as when the thumb is attempting to contact the pinkie finger. In such a case arch-sensing means, e.g., a goniometer, may be used to determine the arch. The measured arch information may then be used along with spatial placement information of a fingertip PSE relative to the metacarpal PSE to determine the spatial placement of the intermediate links. When an arch-sensing means is not employed, the metacarpus may be modeled as a single substantially rigid link.

SJPSs may also be used to allow repositioning or even removal of one or more PSEs while still allowing the multi-articulated structure to be completely determined. For example, referring again to FIG. 11, PSE4 could be removed and the spatial placement of L5 could be determined using spatial information of PSE3 transformed through two goniometers, specifically flex sensors FS2 and FS3. FS2 and FS3 are mounted to the top and side of the wrist joint as shown. FS2 measures the wrist pitch and FS3 measures the wrist yaw. Note, FS2 can rotate about the R7 axis when the wrist yaws and only bends to measure flexure when the wrist pitches. Similarly, FS3 can rotate about the R6 axis when the wrist pitches, but bends to measure the flex when the wrist yaws.

In a similar manner, PSE3 may be replaced by two goniometers, specifically FS2 and FS3, and these goniometers used to transform the relative spatial placement of PSE1 in the PSE4 frame to the frame where PSE3 would otherwise have been positioned. Once transformed, the 4-link problem may be solved as before. In addition to knowing the placement the metacarpus and finger links, the spatial placement of L5 has been measured directly.

Figure 12A:
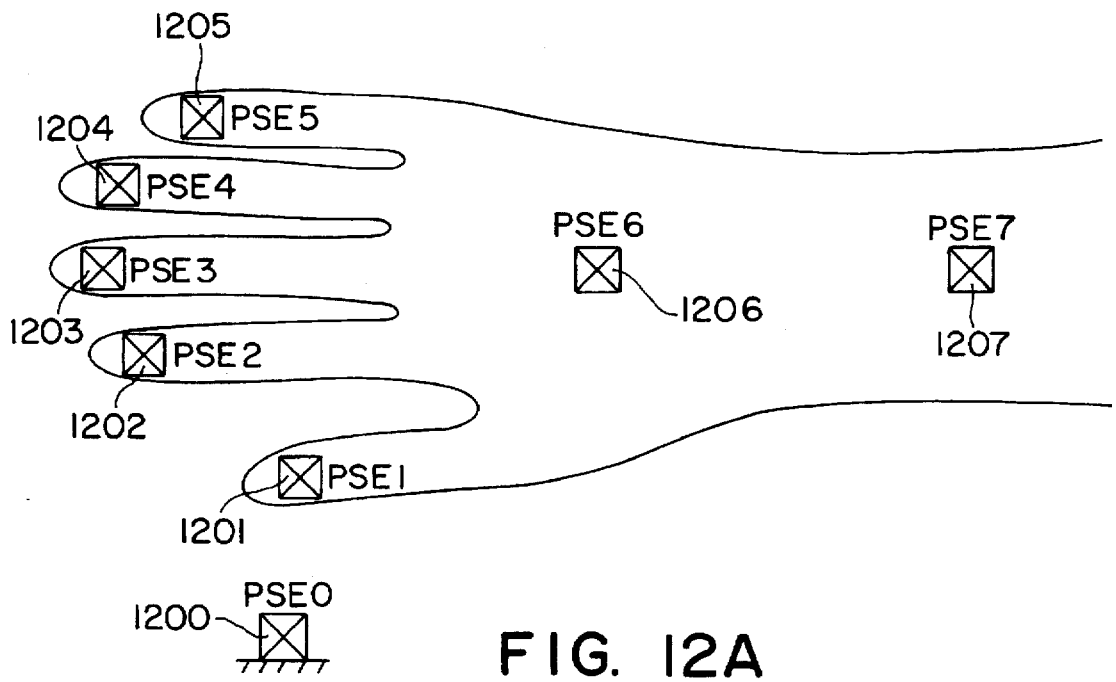
FIG. 12A is a plan view of locations for instrumenting a hand with sensors.

FIG. 12A shows a plan view of preferred locations when instrumenting a hand with PSEs. As shown, there is a PSE (1201–1205) at each fingertip, a PSE (1206) on the metacarpus, a PSE (1207) located on the forearm below the wrist joint and a PSE (1200) affixed to a reference location separate from the hand. A subset of the fingertip PSEs may be used, the subset depending on which of the finger spatial placements are desired. A useful embodiment comprises a PSE on the thumb, a PSE on the index finger, a PSE on the metacarpus and optionally comprises a reference PSE placed external to the hand. Such an embodiment may be used when only a pinching motion of the hand is desired to be measured. This measurement may be used, for example, to control a graphic hand or graphic or physical gripper to pick up a graphic (virtual) object. The embodiment may further include a PSE on the middle finger. Such an embodiment would allow further measurement to be used for control of the grasping of a graphic object, such as needed when twirling a ball between the fingertips.

A useful embodiment may employ two PSEs on the hand (and optionally one PSE external to the hand) along with goniometers to allow determination of the spatial placement of relevant links of the fingers, hand and forearm. In one embodiment the two PSEs may be located on the thumb and index fingers. The motivation for this placement is that there are many applications that desire a graphic hand model to be controlled by a human hand. In such applications it is often important that the relative spatial placements of the tips of the thumb and index fingers be accurately determined so, for example, when the human touches the tips of his/her physical thumb and index finger, the graphic thumbtip and index fingertip correspondingly touch. The embodiment also provides a sufficient number of SJPSs, e.g., flex-sensing goniometers, such that the spatial placement of other relevant links of the thumb and index fingers, and optionally, relevant links of other fingers, the metacarpus and forearm may be determined.

In another useful embodiment, the two PSEs are located one on the thumb tip and one on the metacarpus. The motivation for this placement includes providing an accurate spatial placement of the thumb. For a variety of reasons, it is difficult to use goniometers, specifically flex sensors, to measure the various articulations of the thumb. One reason for the difficulty in employing flex sensors to measure the thumb is the abundant amount of soft tissue near the region where the flex sensors need to be placed. Other reasons why goniometers are difficult to use near the thumb include the way thumb articulations couple, and the lack of efficient and effective goniometer mounting sites. The present embodiment may also provide also provides for optional goniometers to be employed to determine the spatial placement of relevant links of the other four fingers. Note that goniometers normally provide data which more accurately determines the spatial placement of the four fingers than the spatial placement of the thumb. For further details on using goniometers to measure placement of various links of the hand, refer to U.S. Pat. No. 5,047,952 of Kramer, et al.

The embodiment which places PSEs directly on the thumbtip and index fingertip to measure their spatial placement offers opportunity to provide a more accurate measurement than an embodiment which includes a single PSE on the metacarpus or forearm and then uses goniometers to determine the spatial placement of the fingertips. For example, when the PSE is placed on the metacarpus, any errors in using goniometers to measure the various joint angles between the metacarpus and the fingertip may combine additively. Since different goniometers are used to measure the joints of the different fingers, errors in the placements of the individual fingertips may also add to produce an even larger error in the placements of the fingertips relative to each other. When PSEs are located at the fingertips, there is only one measurement needed for each fingertip relative to a reference PSE. If spatial placement of the fingertips relative to a reference location is not needed, one fingertip may be measured relative to the other fingertip directly where one fingertip PSE may be a Tx and the PSE on the other fingertip may be the associated Rx. Such a measurement embodiment offers opportunity to provide spatial placement determinations which are higher in resolution and less contaminated by noise. The configuration of the PSEs and goniometers specifically chosen for an application will be influenced by the relative accuracies, dynamic response, resolution, noise, etc., of PSE and goniometric measurements and how the relative differences affect the final spatial determinations.

The concept of "placing PSEs on the thumbtip and index fingertip, while eliminating the PSE on the metacarpus and including SJPSs to provide additional information," may be extended, for example, to placing PSEs on other fingertips (or important body-parts).

Figure 12B:
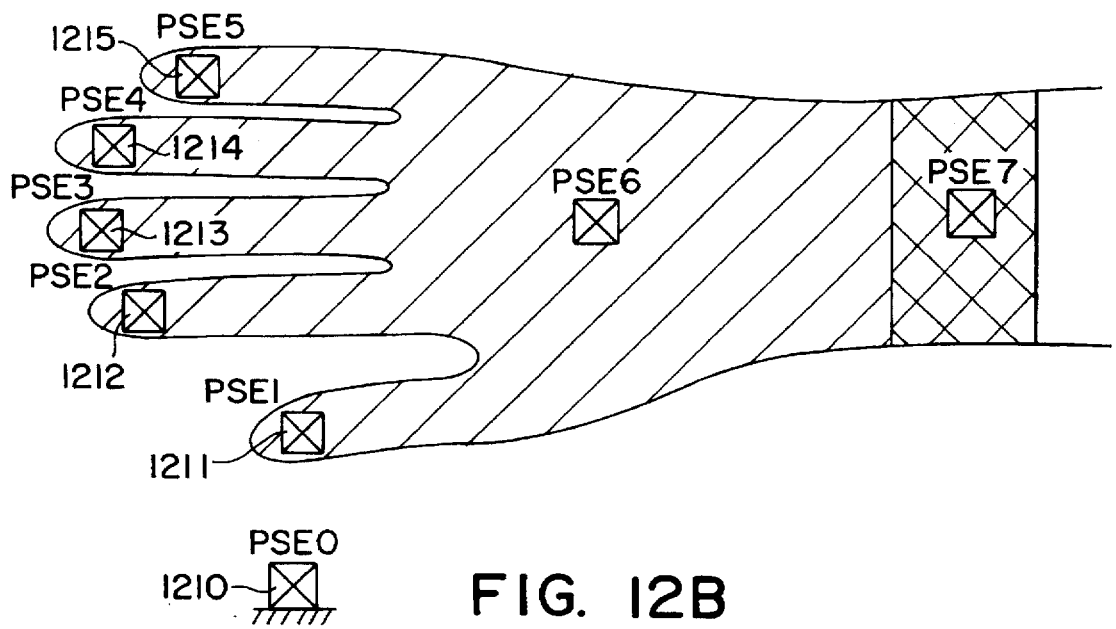
FIG. 12B is a plan view of locations for instrumenting a hand with sensors applied to a glove support.

FIG. 12B shows the PSEs (1200–1207) of FIG. 12A, now shown affixed to a support material (1210–1217). The support 1218 may take the form of a glove, but one or more portions of the glove may be removed if not necessary for PSE support, to increase comfort, tactile sensitivity, ventilation and the like. Portions most likely to be removed from a glove-like support material are the palm, the fingertips and behind plastic, cotton, nylon, Terry Cloth and the like. PSEs may be woven into or the knuckles. Support material may be of a "fish-net" structure. Support material is preferably elastic and may be made of Lycra™, Spandex™ and the like, but may also be made of any other suitable material such as sewn to the support material, they may be glued, attached using Velcro™, screwed onto the material, injection molded into the support, etc. When a glove-like support is used, PSE7 may be affixed to a wristband which extends past the wrist joint onto the forearm. The PSE cables may be affixed to and routed on either side of the support material. Two layers of support material may be used, especially on the top side of the hand, and the PSE cables routed between the two layers, preferably exiting a glove-like support near the wrist region.

Figure 12C:
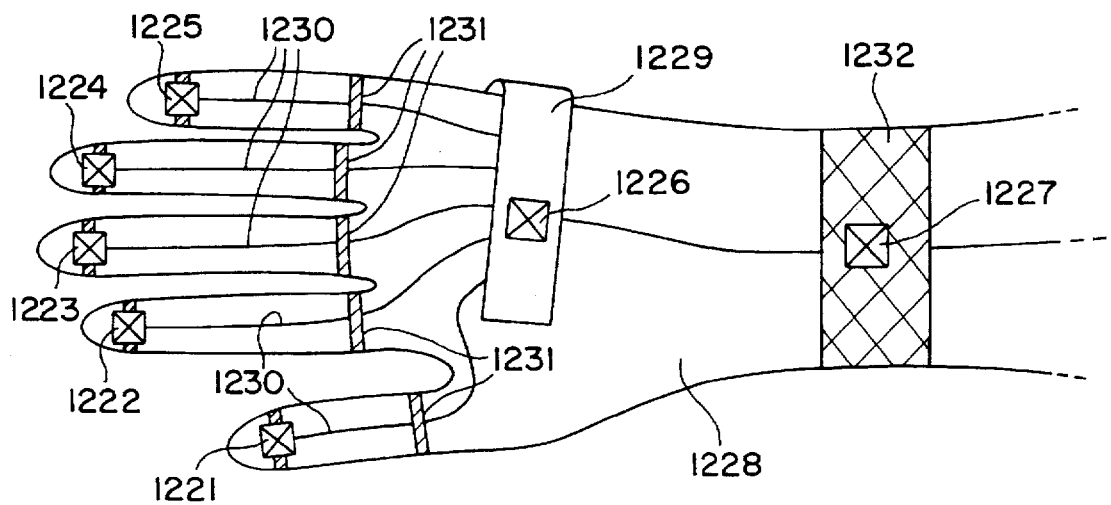
FIG. 12C is a plan view of a hand with sensors affixed to the fingertips and wrist and a sensor affixed to the metacarpus with a U-shaped clip.

FIG. 12C shows a plan view of a hand 1228 with the PSEs (1221–1225, 1227) affixed to the fingertips and wrist via elastic bands and a PSE 1226 affixed to the metacarpus via a U-shaped clip 1229. In the figure the wires 1230 to the fingertip PSEs pass through and are supported by the clip structure 1231 and then are supported by the wrist PSE support structure 1232. At any point on the way back to the electronics unit 102 (which produces the signal transmitted by the Tx and processes the signal received by the Rx) one or more Rx and Tx cables may be combined into a single cable. Such a combination is shown in FIG. 12C as occurring at the U-shaped clip.

Figure 13B:
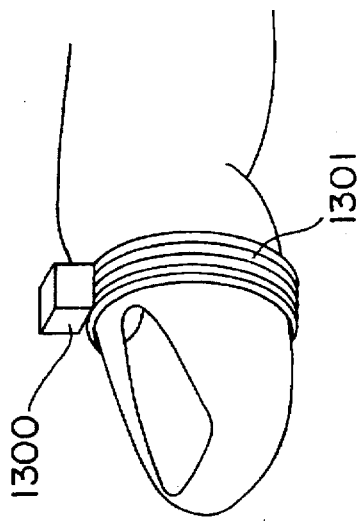
FIGS. 13A and B are views of a sensor on a finger-mount "off" and "on" a finger.
Figure 13A:
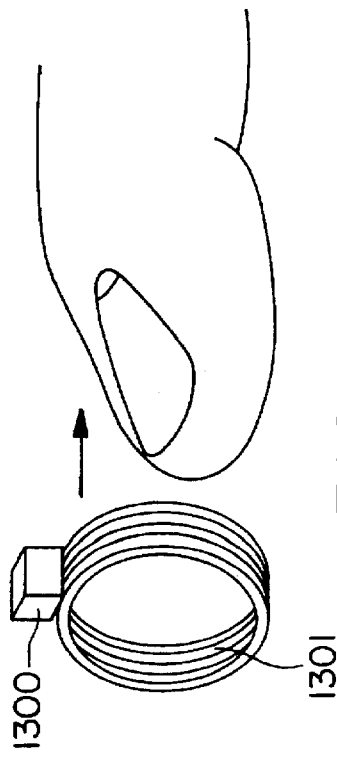

There are a large number of means whereby the PSEs may be affixed to the various portions of the hand and body. FIGS. 13–19 illustrate a few. FIGS. 13A–13B show the PSE 1300 affixed to a band 130. The band is preferably elastic. This embodiment may be used to hold PSEs in juxtaposition to fingers, the metacarpus, the wrist, the forearm, the biceps, the head, the face, the neck, the shoulder, the chest, the back, the waist, the hip, the thigh, the calve, the ankle, the foot, the toes and the like.

Figure 14B:
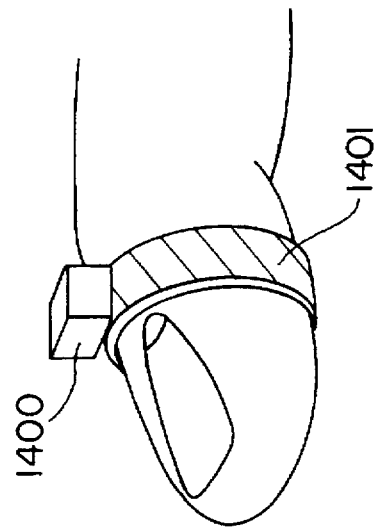
FIGS. 14A and B are views of a sensor on an alternative finger-mount "off" and "on" a finger.
Figure 14A:
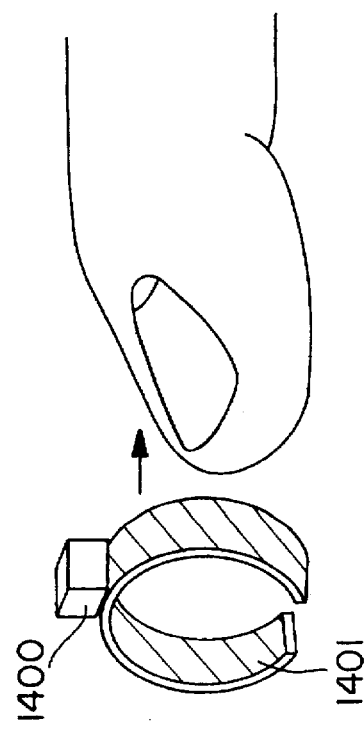

FIGS. 14A and 14B show the PSE 1400 affixed to a clip structure 1401. The clip is preferably formed from a flexible material and may be formed from plastic, metal, fiberglass, wood, glass and the like. The clip support may be used to hold the PSE in juxtaposition to many of the same body locations as the band of FIGS. 13A and 13B.

Figure 15A:
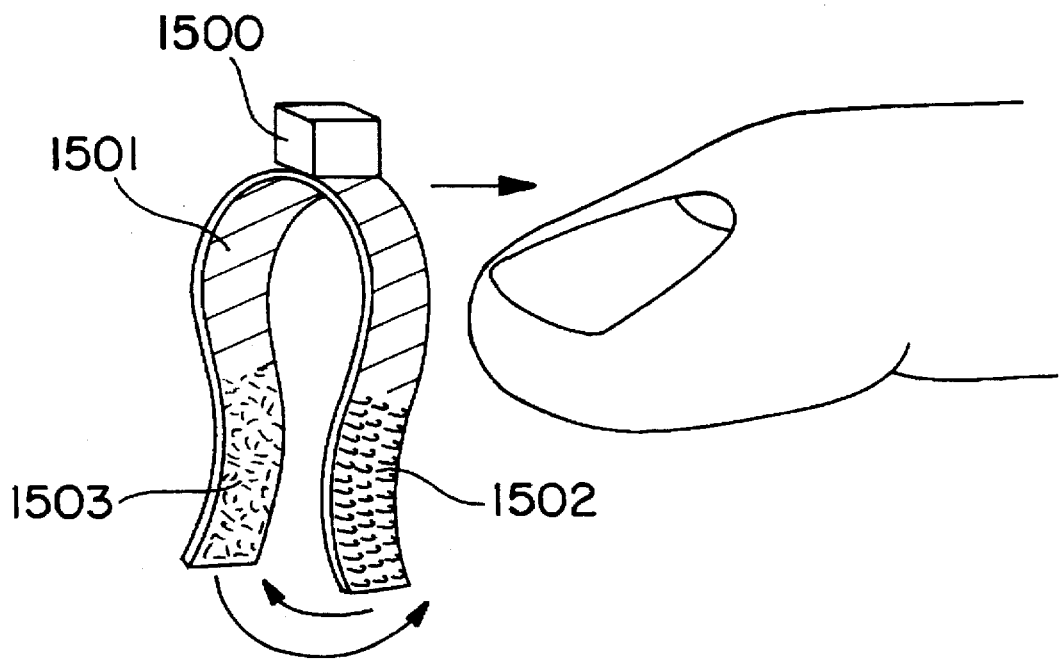
FIGS. 15A and B are views of a sensor on a third alternative finger-mount "off" and "on" a finger.
Figure 15B:
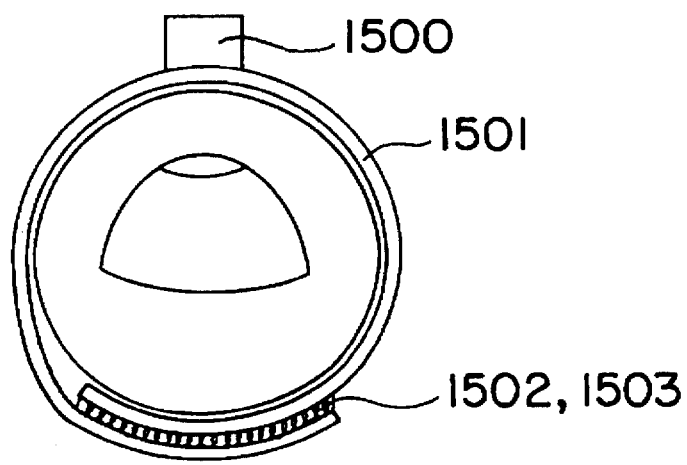

FIGS. 15A and 15B show a PSE 1501 affixed to a strap-like support which possesses hook velcro on one end of the strap 1502 and cotton velcro on the other end 1503. The strap may contain a portion of an elastic material. The strap may be placed around a body part and the velcro portions of the strap connected. The strap support may be used to hold the PSE in juxtaposition to many of the same body locations as the band of FIG. 13A and 13B.

Another useful embodiment comprises a PSE affixed to a buckle support. The buckle straps may contain a portion of elastic material. The buckle strap may be placed around a body part and connected. The buckle support may be used to hold the PSE in juxtaposition to many of the same body locations as the band of FIG. 13A.

Figure 16:
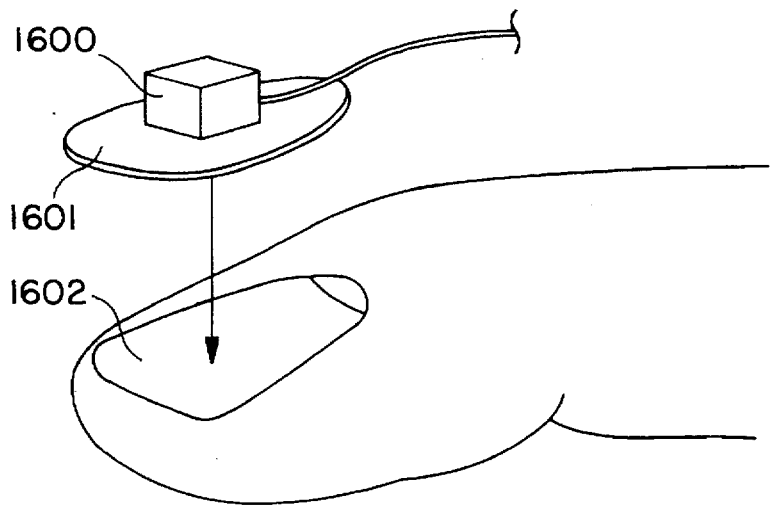
FIG. 16 is a view of a sensor on a fingernail-like mount for affixing the sensor to a finger.

FIG. 16 shows a PSE 1600 affixed to a support 1601 which is then affixed to a portion of the body. In the figure, the support takes the form of a false fingernail which is then adhered to the physical fingernail 1602. The support may be rigid or flexible and may be made from a variety of non-electrically conducting materials such as plastic, wood, glass and the like. The adhesive is preferably of a quick-drying type, and which permits snug adherence to the fingernail and allows removal with reasonable force. The adhesive may also be of the type which must be removed with water or special chemicals. The adhesive support may be used to hold the PSE in juxtaposition to many of the same body locations as the band of FIGS. 13A and 13B.

Figure 17:
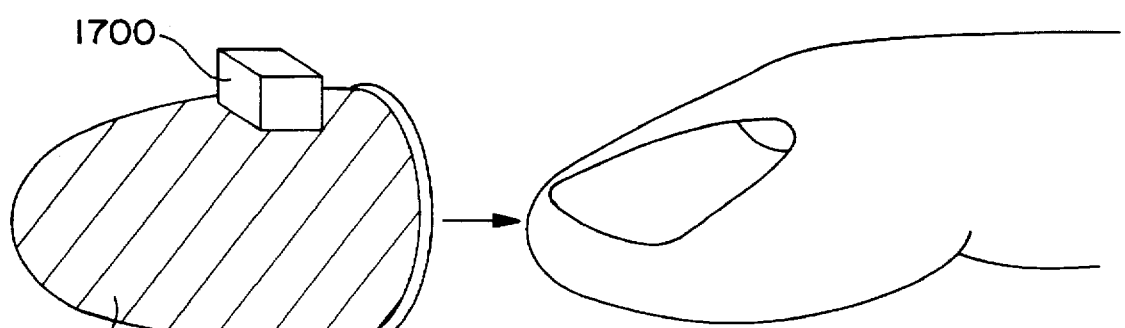
FIG. 17 is a view of a sensor mounted on a thimble-like structure and a partial finger.

FIG. 17 shows a PSE 1700 affixed to a cap-like or thimble-like support 1701 structure. This cap support embodiment may be used to hold a PSE in juxtaposition to body parts such as fingertips, toes and the head. The cap is preferably elastic and may be made from Lycra, Spandex, plastic, nylon, wood, glass and the like.

Figure 18A:
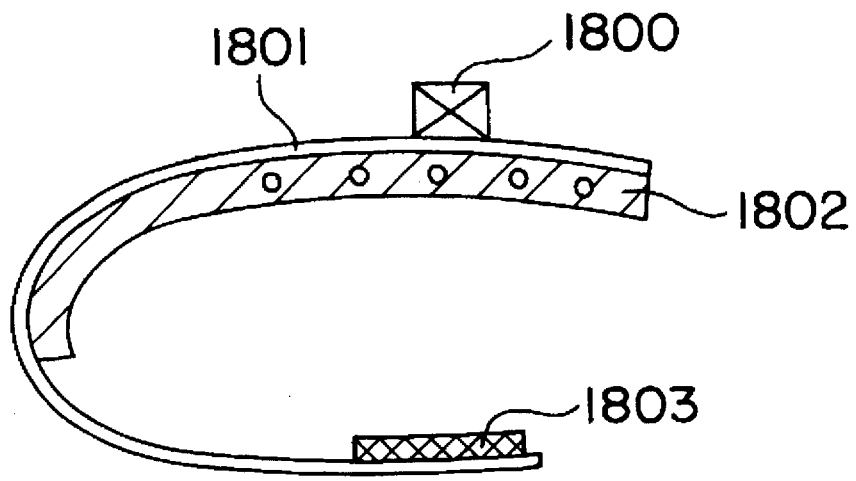
FIGS. 18A and B are end and perspective views of sensors mounted on clip-like structures.
Figure 18B:
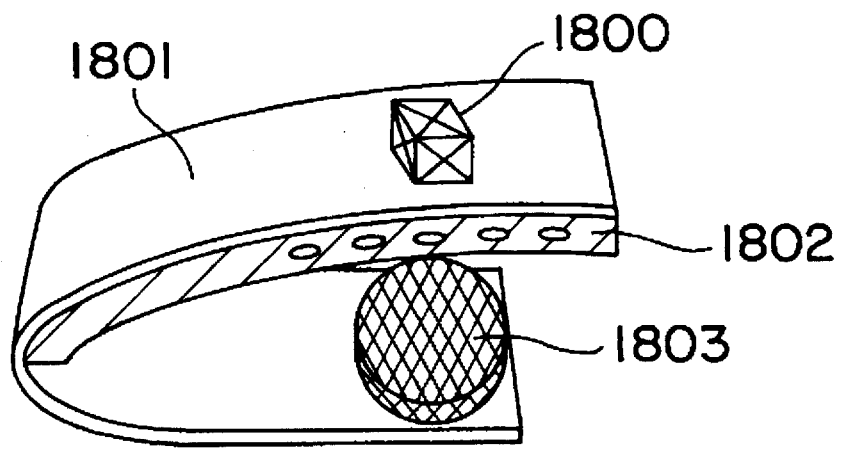

FIGS. 18A and 18B show the end and perspective view for the clip-like structure which may be used to support the PSE 1800 in juxtaposition to the metacarpus and to support the PSE cables. A similar structure may be used to hold a PSE in juxtaposition to any appropriate articulated element. The clip 1801 is preferably flexible and may be made from plastic, wood, glass and the like. The clip may be covered with a foam rubber-like material 1802 to better hold the clip firmly and comfortably to the metacarpus. The palm side of the clip may possess an additional structure 1803, preferably cylindrical in shape, to better hold the clip to the palm. This additional structure may be made from foam rubber, plastic, wood, glass and the like. The PSE cables are preferably routed through 1802 or along the top side of the clip 1801.

Figure 19A:
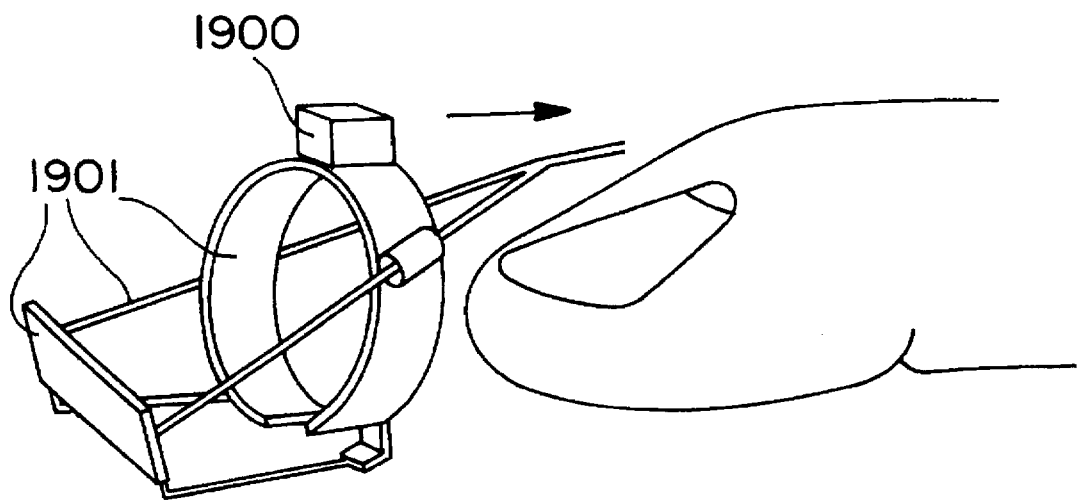
FIGS. 19A and B are perspective views of a sensor mounted on a band with force feedback and mounted on a fingertip.
Figure 19B:
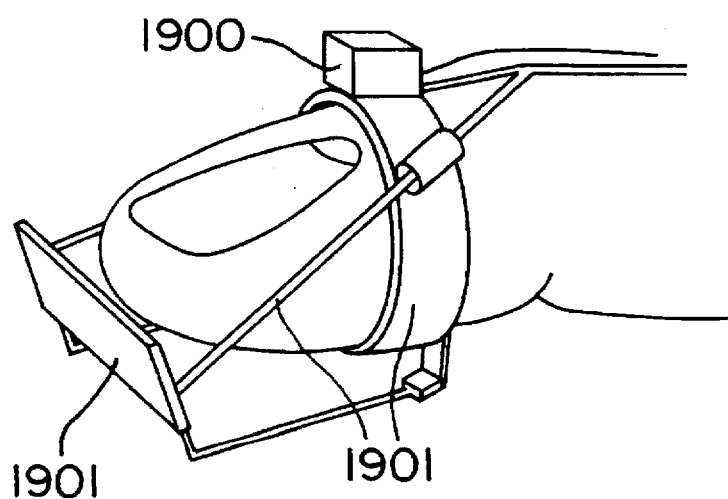
Figure 20A:
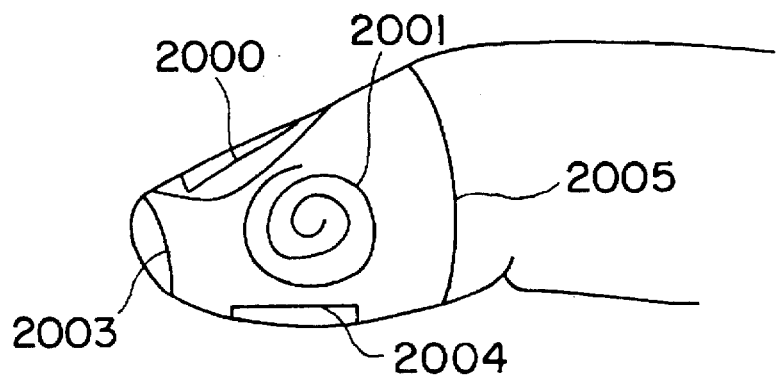
FIGS. 20A, B and C are perspective side, plan and end views of antennae placed at various positions about a finger.
Figure 20B:
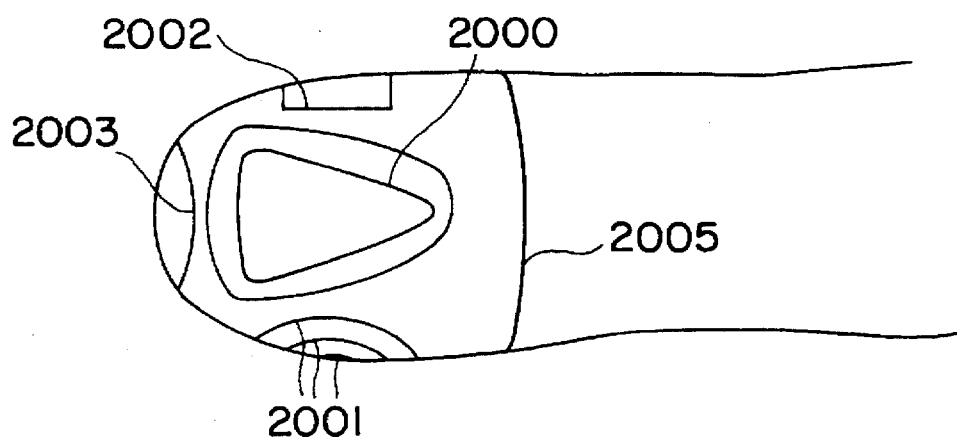
Figure 20C:
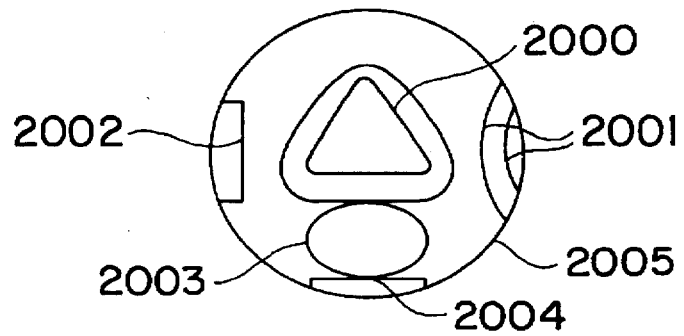

FIGS. 19A and 19B show the PSE 1900 affixed to a support structure 1901 that also supports the apparatus used to apply tactile and force reflection to a fingertip (and in general to any body part). For a detailed description of a "Force Feedback and Texture Simulating Interface Device" refer to international patent application WO 91/11775 by Kramer.

Antennae may be arranged individually about a KCMAS. An individual antenna is arranged in juxtaposition with a link and may be used in combination with one or more other antenna to permit determination of at least one DOF of such link. FIGS. 22A–22C provide the side, plan and end-view of exemplary antennae shapes placements when a finer is one element of the KCMAS. In these Figures, antennae 2000 is placed in juxtaposition to the fingernail, antennae 2001 is placed in juxtaposition to one side of the fingertip, antennae 2002 is placed in juxtaposition to the other side of the fingertip, antennae 2003 is placed in juxtaposition to the end of the fingertip, antennae 2004 is placed in juxtaposition to the pad-side of the fingertip, and antennae 2005 is placed around the fingertip. An embodiment may include one or a plurality of antennae placed on the top and bottom of a finger or other body part, and/or one or a plurality of antennae placed on the sides of a finger or other body-part and/or one or a plurality of antennae placed around a finger or body-part. A preferred embodiment inches three antennae where the normal of one antennae does not lie in the plane of the normals of the other two antennae. A preferred embodiment includes three sufficiently circular antennae where a circular antenna is placed in juxtaposition to a fingernail, a circular antenna is place on a side of the fingertip and a circular antenna is placed around the fingertip. These three antenna serve as an Rx (or Tx) for the fingertip and may act as the PSE2 in the example of FIG. 3.

In some cases, e.g., where the KCMAS is sufficiently constrained or where one or more DOFs is unimportant, a reduced number (as compared to 3 antennae in a preferred embodiment) of antennae may be sufficient. For example, if it is assumed that the fingers can't roll or yaw, then the finger also can't change one of the positional dimensions. As a result, there are only two positional variables and one orientational variable (e.g., the pitch variable) to be determined. Theoretically, three Tx antennae and one Rx antenna should be sufficient to provide the three equations (one equation for each Tx/Rx pair) necessary to solve for the three variable unknowns. A preferred embodiment comprises a single coil positioned on the fingernail and a 3-antennae Tx positioned on the back side of the metacarpus. This sensing embodiment is sufficient to determine the desired 3 DOF.

Additional antennae embodiments exist which may be employed separately or combined to provide advantages under various KCMAS constraint conditions. One preferred embodiment provides two antennae encompassing a body-part. Another embodiment comprises two antennae encompassing a fingertip, two encompassing the metacarpus and two encompassing the forearm below the wrist joint. In this embodiment, when the metacarpal antennae act as Tx's and the finger and wrist antennae act as Rx's, such an embodiment provides the information necessary to determine the placements of the fingertip relative to the metacarpus and the wrist relative to the metacarpus, except when the axes of the antennae on the finger are coaxial with the axes on the metacarpus, finger roll cannot be determined. Yet another embodiment comprises only two antennae, one on each side of a body-part.

Figure 21:
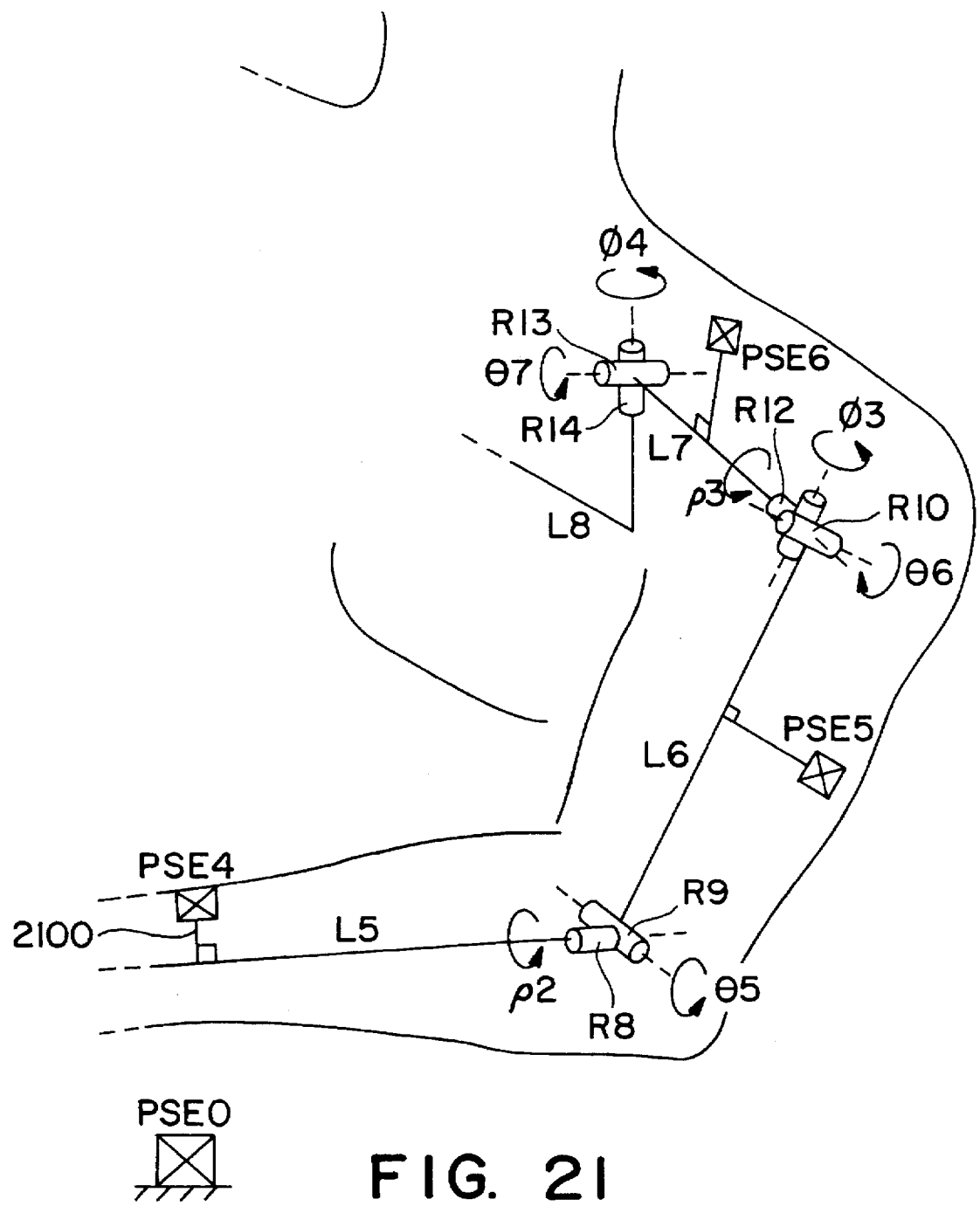
FIG. 21 is a perspective view of the arm and shoulder as a link/revolute KCMAS.

FIG. 21 shows the arm and shoulder modeled as a link/revolute joint KCMAS, as well as preferred locations for PSEs to determine the spatial placements of the inter-connecting links. Using PSE4 affixed to the wrist as before, along with PSE6 affixed to the shoulder region, the spatial placements of links L5, L6 and L7 may be determined, as well as the angular rotations of the various associated revolute joints. One of the two rotary hinge elements of revolute joint R14 is modeled fixed relative to the chest area. Link L7 represents the collar bone (clavicle). In a preferred embodiment, link L7 is measured by PSE6. A preferred location for PSE6 is on the superior surface of the acromial extremity of the clavicle, between the attachments to the deltoid on the anterior border and to the trapezoid on the posterior border. This PSE location is relatively void of soft tissue and thus provides a sufficiently firm mounting site. In general, the link to which a PSE (e.g., PSE4) is associated is specified figuratively by the line (e.g., L5) connecting that PSE to its respective link. As with the 4-link example of FIG. 3, the spatial placement of links L5, L6 and L7 may be determined using spatial information from PSE4, PSE6 and PSE0 using knowledge of the kinematic constraints of relevant body parts.

An alternate configuration which may be used to reduce the number of PSEs (FIG. 11) is to replace PSE6 and PSE4 with PSE5. By using only PSE3 and PSE5, knowledge of the position of the chest (see FIG. 22, PSE7), and kinematic knowledge that the elbow cannot hyperextend, the spatial placements of links L4 (FIG. 11), L5, L6 and L7 may be determined. In one embodiment, PSE5 is affixed to the biceps via an elastic band. The band may allow measurement errors to be introduced since the biceps includes soft tissue and muscle which may vary in placement relative to the link model. Of particular difficulty is measurement of Phi3 using PSE5 due to possible relative motion between PSE5 and the modeled link, L6.

Use of PSE5 may have reduced precision in measurement of shoulder yaw (Phi4) and wrist yaw. If PSE5 is used, it may be preferred to use PSE4 to provide more accurate spatial placement calculations. If accurate shoulder yaw placement coordinates are desired, it may be preferred to use PSE6 in place of PSE5. If the yaw of collar bone link L7 is unimportant, e.g., if angle Phi4 may be assumed fixed, PSE6 may be eliminated and all links and joint angles may be determined using only PSE4 and PSE7, i.e., position information of the chest (see FIG. 22). It should be noted that PSE5 may be used to eliminate ambiguity between rolls Rho2 and Rho3 of links L5 and L6 which may occur when the arm is extended and links L5, L6 and L7 align. Preferably, it may be assumed that there is no drastic change in the ratio of Rho2 and Rho3 from the time just before the three links align to the time when they are aligned and so the ambiguity can be adequately handled. In many cases, if the arm is rolled while fully extended, it may be assumed that the roll is due to R8 (i.e., Rho2). If it is necessary that the arm be rolled while in the extended position and the two angles Rho2 and Rho3 be resolved independently, then PSE5 may be required.

Figure 22:
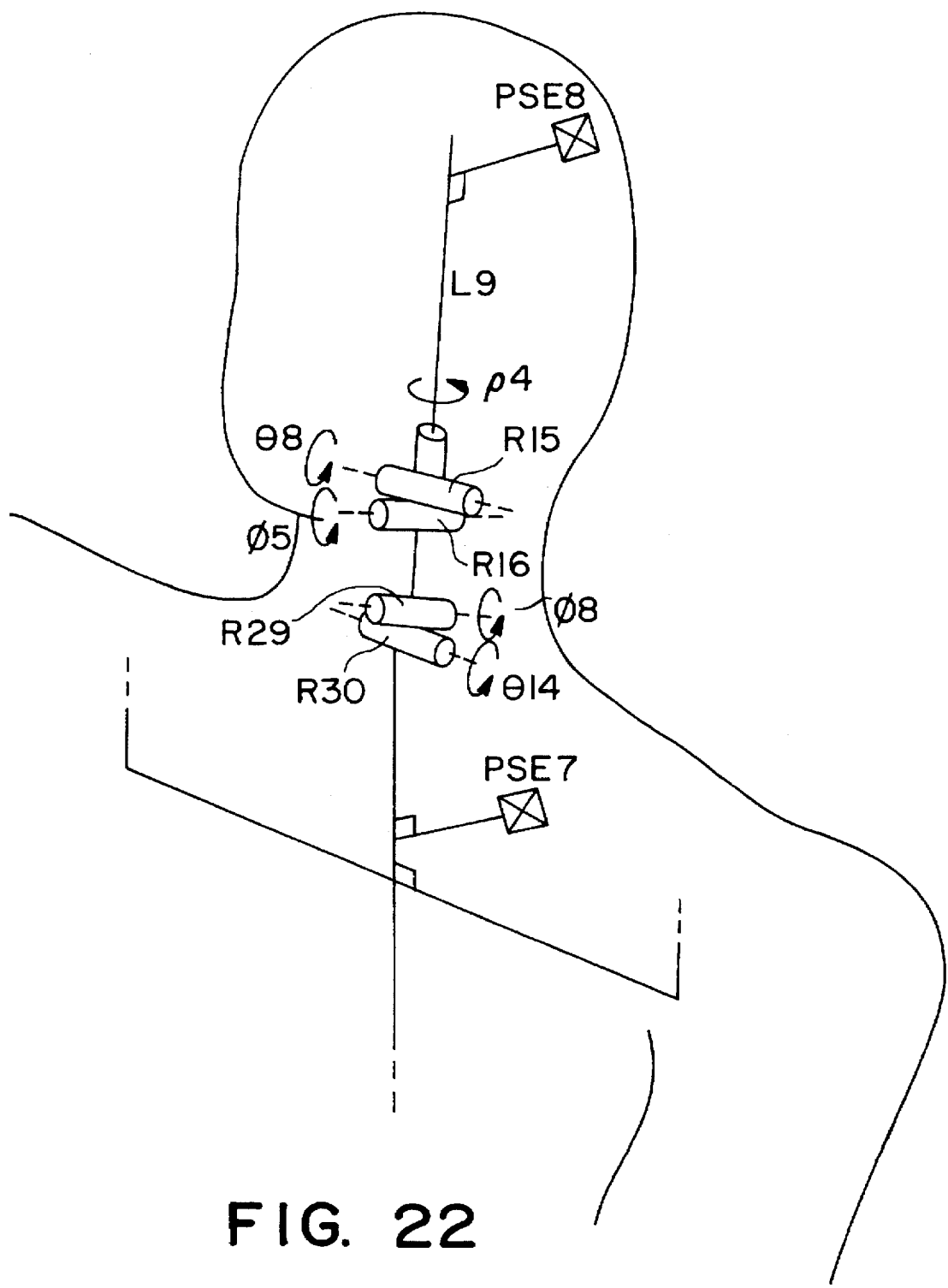
FIG. 22 is a perspective view of the head and neck as a link/revolute KCMAS.
Figure 23:
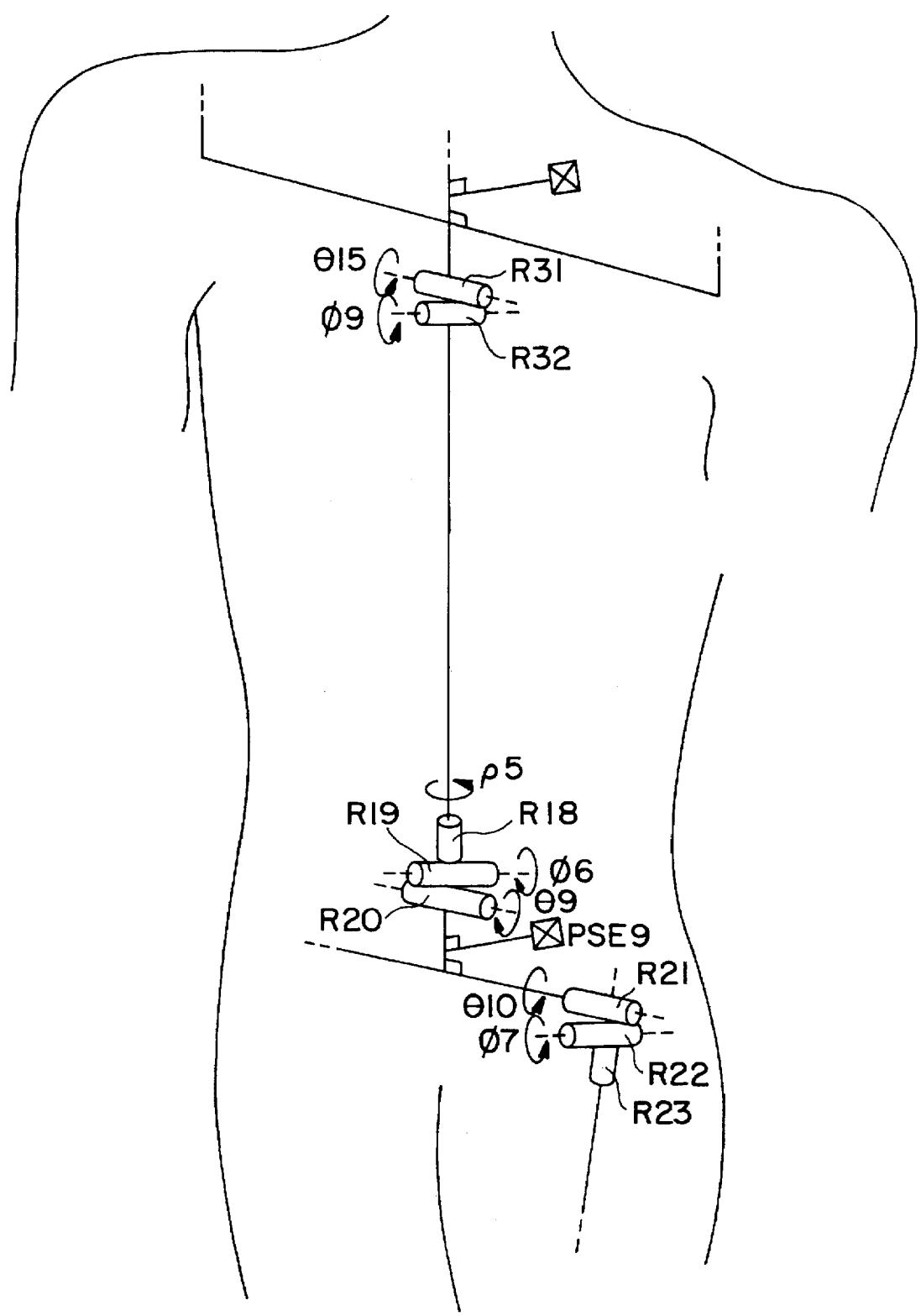
FIG. 23 is a perspective view of the torso and hip as a link/revolute KCMAS.
Figure 24:
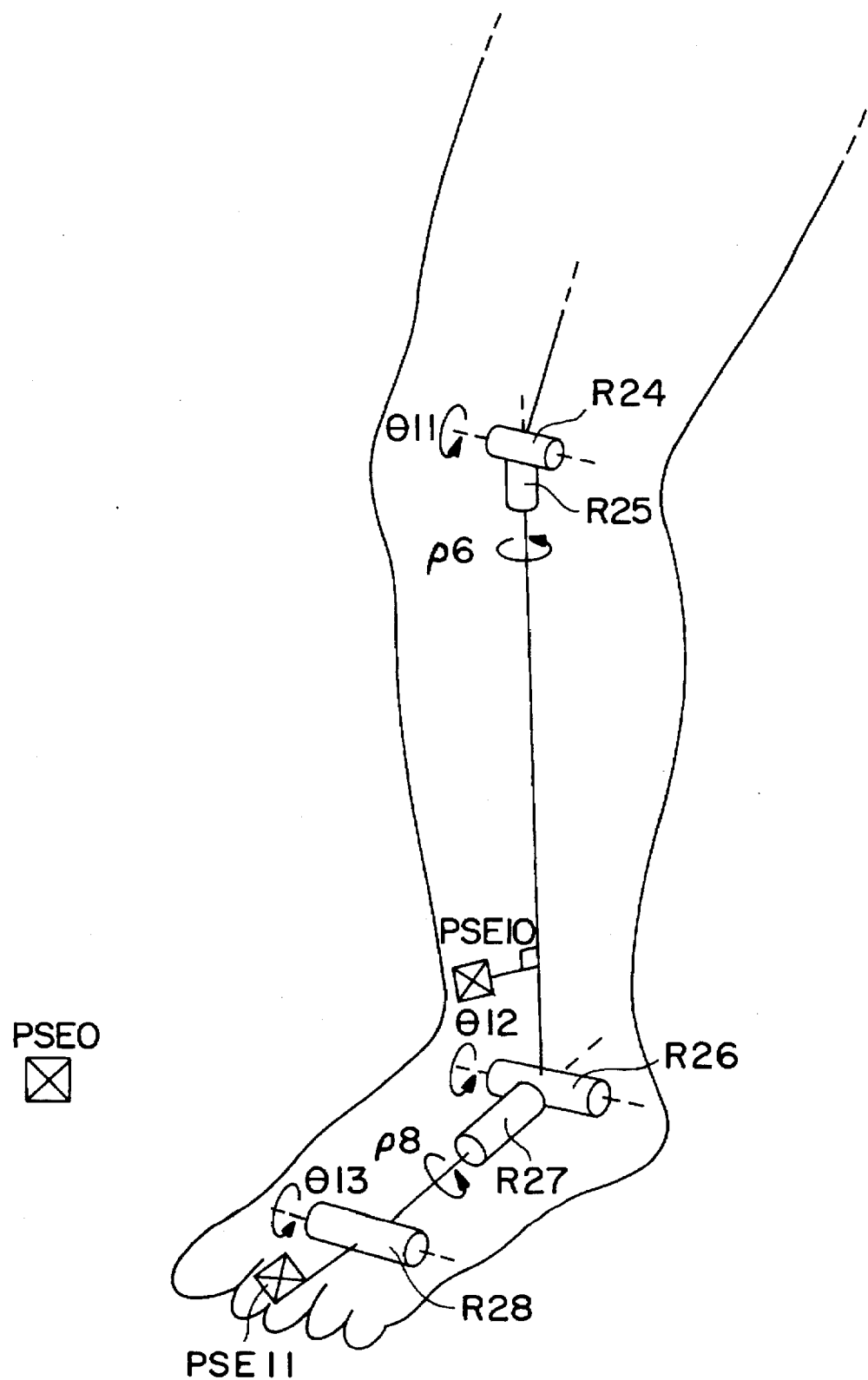
FIG. 24 is a perspective view of the lower portion of the leg as a link/revolute KCMAS.

FIG. 22 shows a revolute joint/link model of the head and neck portion, FIG. 23 the torso and one hip, and FIG. 24 one leg, of a human body. When only one side is shown for clarity, the concept is intended to apply to spatial determination of the articulated elements of the entire body. In FIGS. 22-24, PSEs are shown located beyond the arm and shoulder and are affixed in a preferred embodiment to at least one of the following: the head, upper torso area, pelvis (or hips or waist) area, shin near the ankle, and toes (or instep).

Each of the PSE locations specified in this preferred embodiment was selected to reduce the number of PSEs required while still providing information which will allow the spatial placement of relevant links to be accurately determined. As might be expected, there is more than one way to model the joint structure of the body (and other kinematically constrained multi-articulated structures) and more than one way to choose the positions of the PSEs that will permit determination of the links. The summary joint structure models of FIGS. 22-24, as with the other figures which specifically model the fingers and arm (FIGS. 11 and 21), may be modified as desired to bring out articulations not specifically modeled by the exemplary embodiments, descriptions and figures explicitly provided by the subject application. The specific joint structure model may be modified, while still not deviating from the intent and scope of the subject invention.

FIGS. 25A and 25B provide example support structures for the PSEs affixed to various locations about the body. As described previously in FIGS. 11 and 21-24, the support structures may take on various forms. A preferred embodiment for the head sensor support comprises an elastic headband 2500. A preferred embodiment for the upper torso and shoulder PSE support takes the form of an elastic harness 2501 as shown in FIGS. 25A and 25B. FIGS. 25A and 25B provide a torso harness where PSE5 sensors are used on the biceps in addition to the PSE6 sensors on the shoulder area (2503). The support may comprise velcro or a buckle-like device 2504 to aid donning and doffing. Another preferred embodiment comprises an elastic (e.g., Lycra, Spandex, polyurethane and the like) vest, such as worn by bike racers, speed skaters, scuba divers, women swimmers and the like, where the PSE locations, may be suitably reinforced. The shoulder PSE6 and upper torso PSE7 2505 may be affixed to the harness as shown in FIGS. 25A and 25B.

A preferred pelvic PSE support structure 2506 is also provided in 25A and 25B where the PSE 2507 is located on or near the bony portion at the top of the pelvis near the base of the spine. The support 2506 is again preferred to comprise elastic and/or plastic material and may further comprise velcro or a buckle-like device 2504 to aid in donning and doffing. Another preferred embodiment comprises elastic (e.g., Lycra, Spandex, polyurethane and the like) pants or leggings, such as worn by bike racers, speed skaters, scuba divers and the like, where the PSE locations may be suitably reinforced.

FIGS. 25A and 25B also provide additional example PSE support structures for the shin and feet. The supports may comprise elastic and/or plastic material and/or various other materials and take various forms as described in FIGS. 12-19. One embodiment of these sensors specifies that the supports comprise elastic bands which are pulled over the feet and/or toes (and/or instep). Another embodiment specifies that the shin 2508 and toe 2509 PSEs be affixed to elastic stockings 2510 for easy and reliable donning and doffing. Note that by affixing PSEs to the toe area, the flex in the "ball" area of the foot may be determined. The PSE may be moved nearer to the instep area to provide only ankle angular information. If the toes are always in contact with the ground the flex in the ball area of foot can still be determined using the ground to provide the needed constraint. If the toes are allowed to leave the ground, using the instep PSE in place of the toe PSE will result in not being able to determine the ball flex.

There is a slight roll capability in the knee joint R25 (Rho7). Normally since this capability is so slight this roll joint may be ignored and all roll in the foot relative to the pelvis may be attributed to R23 (Rho6). If R25 must be modeled explicitly, an additional PSE on the thigh may be employed so the two roll angles, Rho6 and Rho7, can be differentiated.

Figure 26:
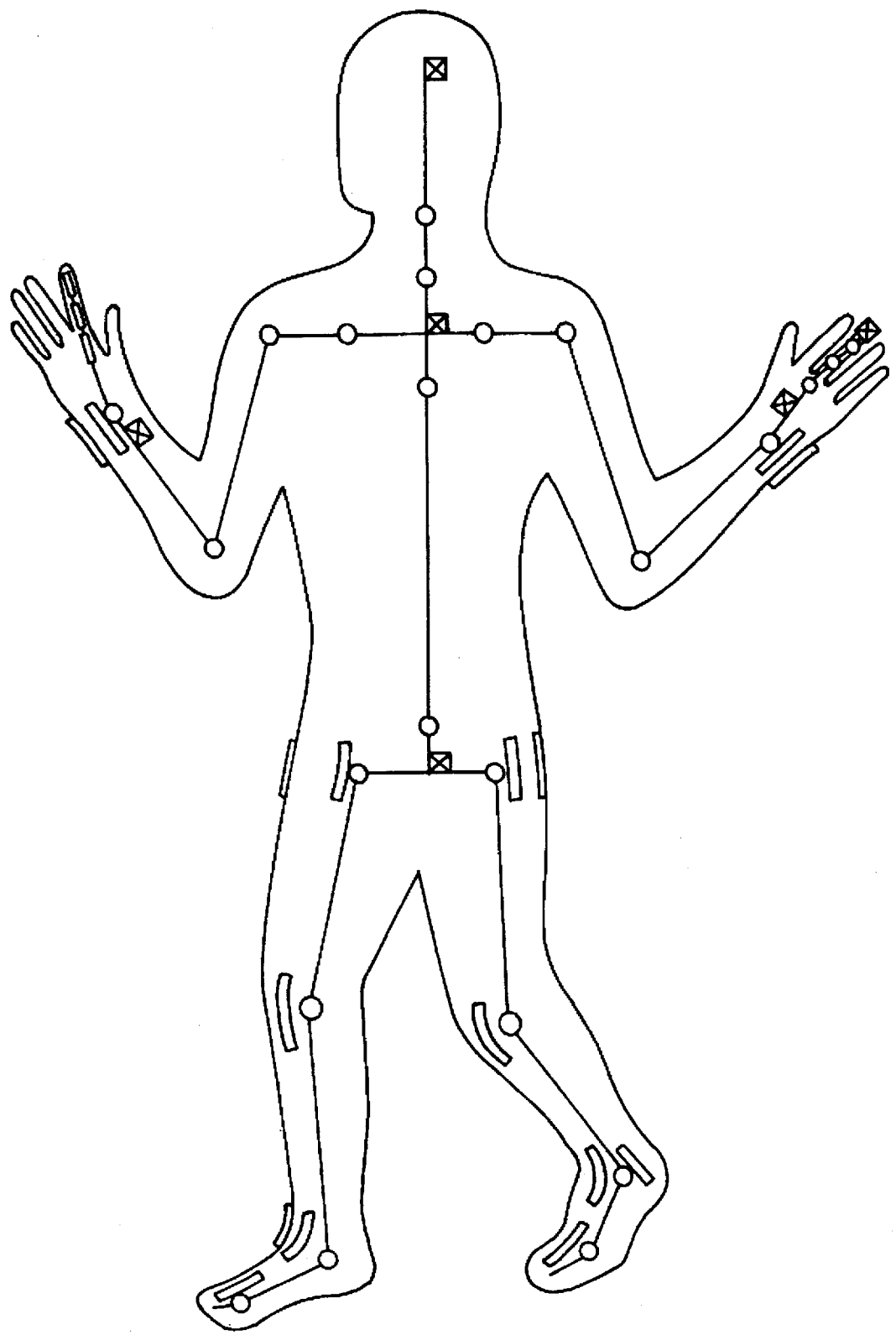
FIG. 26 is a diagrammatic body view indicating spatial placements of sensors at various links.

FIG. 26 provides an example embodiment which comprises a combination of PSEs and goniometers to measure the spatial placements of various links of the human body. A preferred goniometer is a variable-resistance flex sensor. The hand on the left side of the body outline in FIG. 26 provides one embodiment for hand-sensing which uses only goniometers for measuring the positions of the fingers relative to the metacarpus. Goniometers are shown only on one finger for clarity. The hand on the right side of the body outline provides one embodiment for hand-sensing which uses only PSEs to measure the positions of the fingers. The PSEs are also shown only on one finger for clarity. The PSE and goniometer placements provided allow determination of relevant body-parts with the exception that roll of the leg and foot cannot be measured and yaw (forward/backward) motion of the shoulder cannot be measured. As described previously, the PSE located on the metacarpus may be located instead and the forward side of the wrist joint. An embodiment which measures many important articulations of a human body, incorporating only PSEs to measure the articulations of the fingers as shown on the hand on the right of the body outline in FIG. 26 requires 15 PSEs (10 PSEs on the fingertips alone) and 14 goniometers. The PSEs on the fingertips may also be replaced by a plurality of goniometers between the PSE placed on the metacarpus (or below the wrist) and the fingertips (as shown on the hand on the left of the body outline in FIG. 26). Such an embodiment requires only 5 PSEs and 54 goniometers (44 for the hands and wrists alone). To contrast, the embodiments of FIGS. 11, 12 and 21-25 requires from 21 to 23 PSEs and no goniometers. The choice of embodiments used will be based on the relative .needs of the user as to the information desired, such information including: accuracy, resolution, latency, bandwidth, size, weight, inertia, noise susceptibility, cost and the like. The three full-body sensing embodiments provide example locations of PSEs and goniometers. Modifications may be made without deviating from the intent and scope of the subject invention.

The formula for constraints and mathematical determination of a class human or other living being body-parts modeled as kinematically-constrained multi-articulated structures offer distinct advantages over known prior-art measurement systems. The subject invention provides means whereby not all links of interest need be directly measured for their spatial placement to be determined. By reducing the number of links which must be directly measured, the resulting measurement system is lighter, less incumbering, has less inertia, generates less heat, produces less raw sensor data and is cheaper. The subject invention provides a means of measurement of body-parts modeled as kinematic ally constrained multi-articulated structures heretofore unavailable. The measurement system may measure the articulations of the hand, arm and many other important articulations of the human body and other living beings.

While the invention has been described with reference to embodiments specific to human body-parts, the description is illustrative of the invention and is not to be construed as limiting the invention. For example, the joint configurations, sensor locations, support structures and mathematical solutions provided are intended to exemplify a class of problems which may be solved using the methodology provided by the subject invention. The joint configurations, sensor locations, support structures and mathematical solutions may be modified to more efficiently determine the defining parameters and model of a multi-articulated structure without deviating from the intended scope of the subject invention.

Any publication or patent described in the specification is hereby included by reference as if completely set forth in the specification.

Various modifications and amplifications may occur to those skilled in the art without departing form the true spirit and scope of the invention as defined by the appended claims.

What is claimed is:

1. A system for determining the spatial position and orientation of a plurality of body parts of a living being, said body parts being individual articulated elements of a kinematically-constrained, multi-articulated structure of at least three links joined by at least two revolute joints where two of the joints are separated by a single link, the system comprising:

a plurality of position-sensing elements for disposition about links of said multi-articulated structure;

means for securing each of said position-sensing elements on a respective link;

first processing means for determining the spatial position and orientation of each of said position-sensing elements and thereby determining the spatial position and orientation of the respective links each position-sensing element is attached to, said first processing means generating an output indicative of the determination; and second processing means for determining the spatial position and orientation of a link located between the links on which a position-sensing element is placed utilizing the output of the first processing means and the kinematic constraints of the articulated elements of said multi-articulated structure, whereby the spatial position and orientation of at least n+1 links can be determined, where n equals the number of links on which a position-sensing element is disposed.

2. The system of claim 1, wherein the kinematically-constrained, multi-articulated structure is a finger and wherein one position-sensing element is adapted to be positioned on a finger phalanx at other than the proximal phalanx and one position-sensing element is adapted to be positioned on the metacarpus.

3. The system of claim 1, further including a reference element.

4. A system for determining the spatial position and orientation of a plurality of body parts of a living being, said body parts being individual articulated elements of a kinematically-constrained, multi-articulated structure of at least four links joined by at least three revolute joints where two of the joints are separated by a single link, the system comprising:

a plurality of position-sensing elements for disposition about links of said multi-articulated structure;

at least one goniometer for disposition about at least one of the revolute joints;

means for securing each of said position-sensing elements on a respective link;

means for securing the at least one goniometer in functional relationship to at least one revolute joint;

first processing means for determining the spatial position and orientation of each of said position-sensing elements and thereby determining the spatial position and orientation of the respective links each position-sensing element is attached to and for determining the angular orientation of the revolute joint about which the goniometer is disposed, said first processing means generating outputs indicative of the determinations; and second processing means for determining the spatial position and orientation of a link located between the links on which a position-sensing element is placed and between joints without a goniometer disposed thereon utilizing the outputs of the first processing means and the kinematic constraints of the articulated elements of said multi-articulated structure, whereby the spatial position and orientation of at least n+1 links can be determined, where n equals the number of links on which a position-sensing element is disposed plus the number of revolute joints on which a goniometer is disposed.

5. The system of claim 4, wherein the kinematically-constrained, multi-articulated structure is a linger and wherein one position-sensing element is adapted to be positioned on a finger phalanx at other than the proximal phalanx and wherein the at least one goniometer is adapted to be disposed about a fingerjoint and one position-sensing element is adapted to be positioned on the metacarpus.

6. The system of claim 4, further including a reference element.

\* \* \* \* \*